US010182793B2

(12) United States Patent
Satoh et al.

(10) Patent No.: US 10,182,793 B2
(45) Date of Patent: Jan. 22, 2019

(54) ULTRASONIC DIAGNOSTIC APPARATUS, IMAGE PROCESSING APPARATUS, AND IMAGE PROCESSING METHOD

(71) Applicant: Toshiba Medical Systems Corporation, Otawara-shi (JP)

(72) Inventors: Shunsuke Satoh, Nasushiobara (JP); Yutaka Kobayashi, Nasushiobara (JP); Tomokazu Fujii, Nasushiobara (JP); Masaru Ogasawara, Nasushiobara (JP); Shogo Fukuda, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 637 days.

(21) Appl. No.: 14/481,414

(22) Filed: Sep. 9, 2014

(65) Prior Publication Data

US 2014/0378835 A1 Dec. 25, 2014

Related U.S. Application Data

(63) Continuation of application No. PCT/JP2013/058651, filed on Mar. 25, 2013.

(30) Foreign Application Priority Data

Mar. 26, 2012 (JP) ................................ 2012-070207
Mar. 25, 2013 (JP) ................................ 2013-062840

(51) Int. Cl.
*A61B 8/00* (2006.01)
*A61B 8/08* (2006.01)
(Continued)

(52) U.S. Cl.
CPC ................ *A61B 8/483* (2013.01); *A61B 8/02* (2013.01); *A61B 8/06* (2013.01); *A61B 8/0891* (2013.01);
(Continued)

(58) Field of Classification Search
USPC ........................................................ 600/441
See application file for complete search history.

(56) References Cited

U.S. PATENT DOCUMENTS 5,669,385 A * 9/1997 Pesque ............... G01S 15/8981
128/916
6,500,118 B1 12/2002 Hashimoto
(Continued)

FOREIGN PATENT DOCUMENTS

CN 101347341 A 1/2009
JP 2000-132664 A 5/2000
(Continued)

OTHER PUBLICATIONS

Combined Office Action and Search Report dated Oct. 28, 2014 in Chinese Patent Application No. 201380000553.0 (with English translation of category of cited documents).
(Continued)

*Primary Examiner* — Joel F Brutus
(74) *Attorney, Agent, or Firm* — Oblon, McClelland, Maier & Neustadt, L.L.P.

(57) ABSTRACT

An ultrasonic diagnostic apparatus according to an embodiment includes an acquiring unit and a detecting unit. The acquiring unit acquires fluid volume data representing fluid information related to a fluid flowing through a scan region that is a region three-dimensionally scanned by ultrasonic. The detecting unit detects a region that is a fluid existing region in the scanned region using the fluid information, and detects an inner cavity region of a lumen in volume data to be applied with image processing using the region thus detected.

15 Claims, 16 Drawing Sheets

(51) Int. Cl.

| | |
|---|---|
| ***A61B 8/06*** | (2006.01) |
| ***G01S 15/89*** | (2006.01) |
| ***A61B 8/02*** | (2006.01) |
| *A61B 6/00* | (2006.01) |
| *G01S 7/52* | (2006.01) |
| *A61B 8/04* | (2006.01) |

(52) U.S. Cl.

CPC .............. *A61B 8/466* (2013.01); *A61B 8/488* (2013.01); *A61B 8/523* (2013.01); *A61B 8/5223* (2013.01); *G01S 15/8988* (2013.01); *G01S 15/8993* (2013.01); *A61B 6/504* (2013.01); *A61B 6/5247* (2013.01); *A61B 8/04* (2013.01); *A61B 8/0833* (2013.01); *A61B 8/0883* (2013.01); *A61B 8/4254* (2013.01); *A61B 8/463* (2013.01); *A61B 8/486* (2013.01); *A61B 8/5207* (2013.01); *A61B 8/5246* (2013.01); *A61B 8/5261* (2013.01); *A61B 8/543* (2013.01); *G01S 7/52074* (2013.01); *G01S 7/52087* (2013.01)

(56) References Cited

U.S. PATENT DOCUMENTS 6,663,568 B1 * 12/2003 Gill .......................... A61B 8/06 600/454
2005/0124885 A1 * 6/2005 Abend .................... A61B 8/06 600/443
2005/0283075 A1 * 12/2005 Ma ...................... G01S 15/8979 600/441
2007/0032725 A1 * 2/2007 Watanabe .......... A61B 5/02007 600/437
2007/0149877 A1 * 6/2007 Oshiki .............. A61B 5/02007 600/427
2009/0024029 A1 1/2009 Murashita
2009/0137907 A1 5/2009 Takimoto et al.
2010/0215225 A1 * 8/2010 Kadomura ............ G06T 7/0012 382/128
2011/0018871 A1 * 1/2011 Shirahata ................ A61B 8/00 345/419
2011/0221756 A1 9/2011 Inoue et al.

FOREIGN PATENT DOCUMENTS

JP 2008-148858 A 7/2008
JP 2009-022342 A 2/2009
JP 2009-125280 A 6/2009
JP WO 2010/055817 A1 5/2010
JP 2012-040207 A 3/2012

OTHER PUBLICATIONS

Office Action dated Sep. 20, 2016 in Japanese Patent Application No. 2013-062840.
International Search Repot dated May 7, 2013 for PCT/JP2013/058651 filed on Mar. 25, 2013 with English Translation.
International Written Opinion dated May 7, 2013 for PCT/JP2013/058651 filed on Mar. 25, 2013.

* cited by examiner

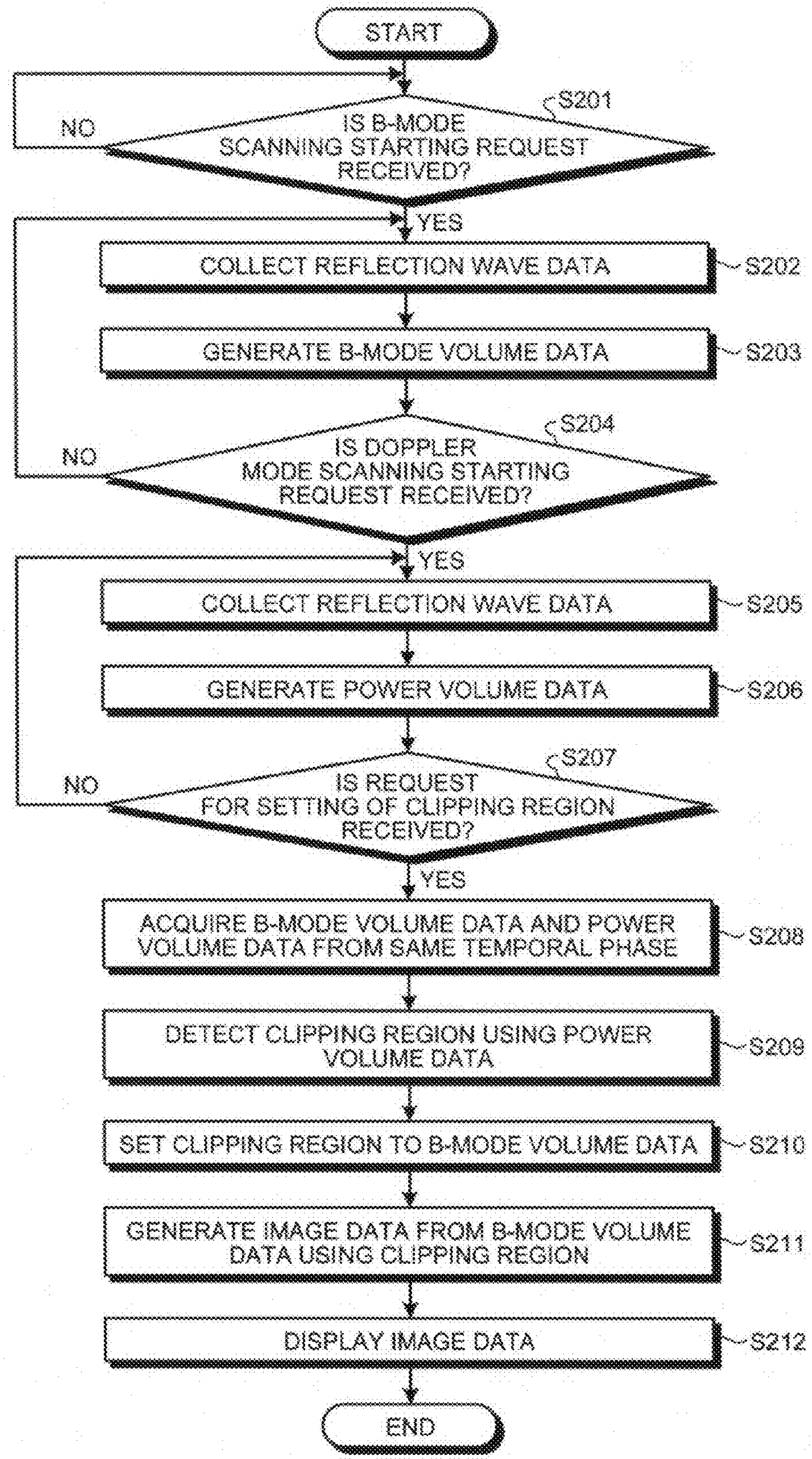
FIG.11
START
IS B-MODE SCANNING STARTING REQUEST RECEIVED?
S201
NO
YES
COLLECT REFLECTION WAVE DATA
S202
GENERATE B-MODE VOLUME DATA
S203
IS DOPPLER MODE SCANNING STARTING REQUEST RECEIVED?
S204
NO
YES
COLLECT REFLECTION WAVE DATA
S205
GENERATE POWER VOLUME DATA
S206
IS REQUEST FOR SETTING OF CLIPPING REGION RECEIVED?
S207
NO
YES
ACQUIRE B-MODE VOLUME DATA AND POWER VOLUME DATA FROM SAME TEMPORAL PHASE
S208
DETECT CLIPPING REGION USING POWER VOLUME DATA
S209
SET CLIPPING REGION TO B-MODE VOLUME DATA
S210
GENERATE IMAGE DATA FROM B-MODE VOLUME DATA USING CLIPPING REGION
S211
DISPLAY IMAGE DATA
S212
END FIG.13
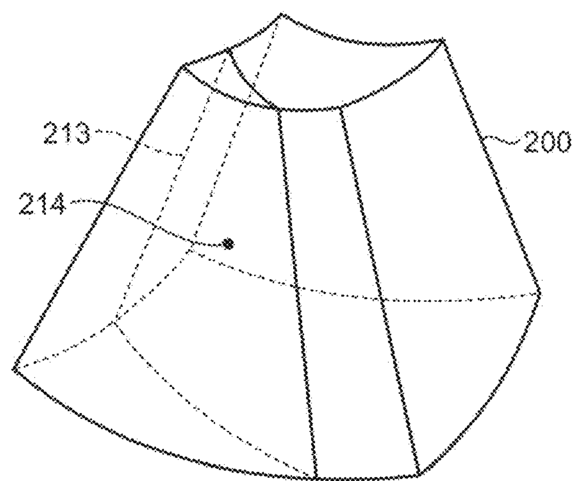
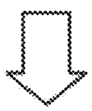
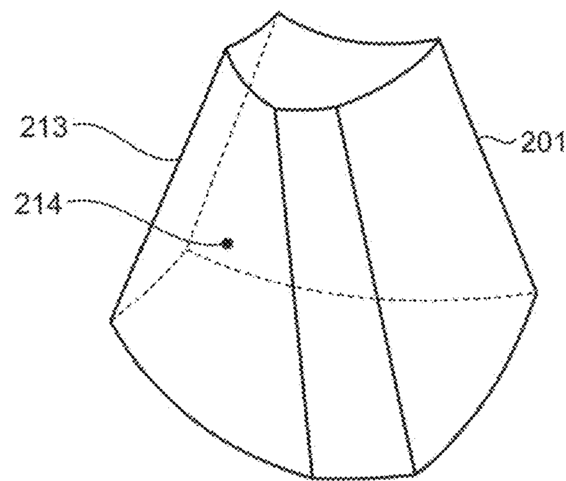
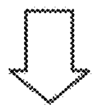
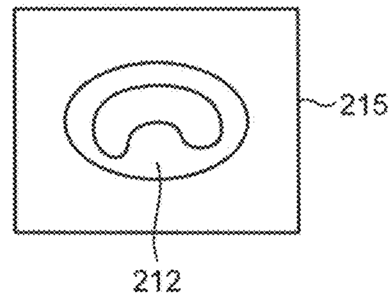

FIG.14
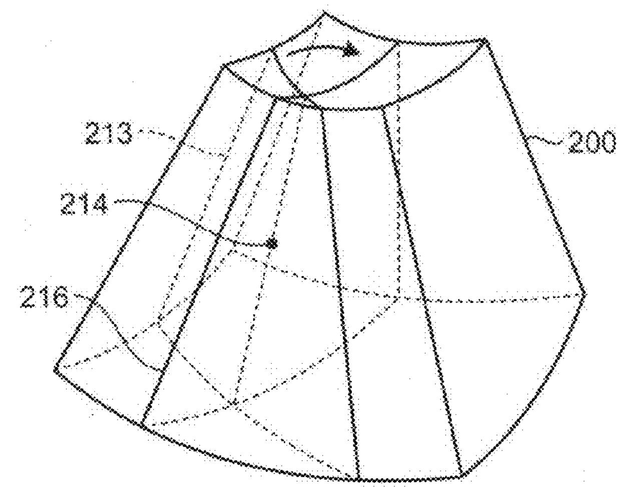
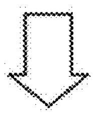
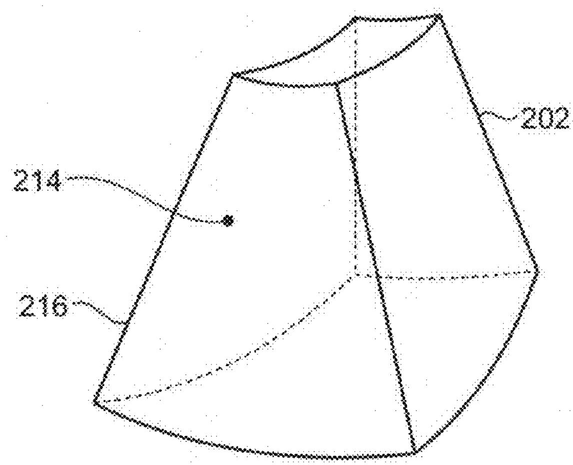
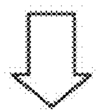
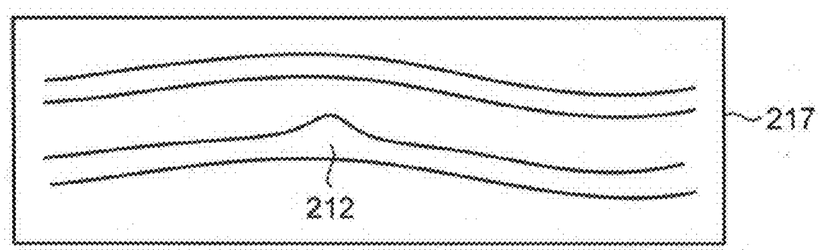

ULTRASONIC DIAGNOSTIC APPARATUS, IMAGE PROCESSING APPARATUS, AND IMAGE PROCESSING METHOD

CROSS-REFERENCE TO RELATED APPLICATIONS

This application is a continuation of PCT international application Ser. No. PCT/JP2013/058651 filed on Mar. 25, 2013 which designates the United States, incorporated herein by reference, and which claims the benefit of priority from Japanese Patent Application No. 2012-070207, filed on Mar. 26, 2012 and Japanese Patent Application No. 2013-062840, filed on Mar. 25, 2013, the entire contents of which are incorporated herein by reference.

FIELD

Embodiments described herein relate generally to an ultrasonic diagnostic apparatus, an image processing apparatus, and an image processing method.

BACKGROUND

A conventionally known example of a displaying technique that allows the inside of a lumen to be observed is a fly-through view with virtual endoscopic (VE) images. Such a fly-through view uses three-dimensional medical image data (volume data) including a luminal tissue. A VE image is an image that is generated from volume data using a perspective projection from a viewpoint position and a line of sight set inside of a lumen. A fly-through view is a technique for displaying VE images at different view positions as dynamic images, by shifting the viewpoint position along the center line (central line) of the lumen. Fly-through views are mainly used for volume data including digestive organs such as a large intestine acquired using an X-ray computed tomography (CT) apparatus or a magnetic resonance imaging (MRI) apparatus.

Recently having been put in practical use is an ultrasonic diagnostic apparatus that generates volume data along a time sequence approximately in real time, using an ultrasonic probe that can perform three-dimensional ultrasonic scanning. In the field of ultrasonic examinations as well, fly-through views using B-mode volume data including luminal tissues have come to become implemented increasingly. However, because of the nature of an ultrasonic diagnostic apparatus, an ultrasonic diagnostic apparatus is not suitable for observations of organs such as digestive organs not filled with water or substance. Hence, fly-through views using an ultrasonic diagnostic apparatus have been applicable to a lumen filled with fluid, e.g., a blood vessel filled with blood, or a bile duct filled with bile.

An ultrasonic diagnostic apparatus is a medical image diagnostic apparatus having a higher representation resolution for microstructures, compared with other medical image diagnostic apparatuses such as an X-ray CT apparatus and an MRI apparatus, and is useful for observing the circulatory system, mainly blood vessels. For example, a fly-through view of a blood vessel using an ultrasonic diagnostic apparatus is useful as a new approach for observing a circulatory disease such as hemadostenosis or an aneurysm. When a fly-through view of a lumen is to be provided, the inner wall of the lumen will be the clipping region, which will be the target of rendering.

However, contours between structures tend to blur more in an ultrasonic image (B-mode image) than in other types of medical image such as an X-ray CT image or an MRI image. Therefore, it has been difficult to use a computer program to automatically detect the inner cavity region of a lumen in B-mode volume data, unless the lumen has a certain diameter or larger. Therefore, a fly-through view in an ultrasonic diagnostic apparatus is currently limited to a tubular tissue having a certain diameter or larger, and it has been difficult to apply a fly-through view to thin tubular structures.

BRIEF DESCRIPTION OF THE DRAWINGS

FIG. 11 is a flowchart for explaining an exemplary process performed by the ultrasonic diagnostic apparatus according to the second embodiment;

FIG. 13, FIG. 14, and FIG. 15 are schematics for explaining the image generator according to the third embodiment;

DETAILED DESCRIPTION

An ultrasonic diagnostic apparatus according to an embodiment includes an acquiring unit and a detecting unit. The acquiring unit acquires fluid volume data representing fluid information related to a fluid flowing through a scan region that is a region three-dimensionally scanned by ultrasonic. The detecting unit detects a region that is a fluid existing region in the scanned region using the fluid information, and detects an inner cavity region of a lumen in volume data to be applied with image processing using the region thus detected.

An ultrasonic diagnostic apparatus according to some embodiments will now be explained in detail with reference to the accompanying drawings.

First Embodiment

Figure 1:
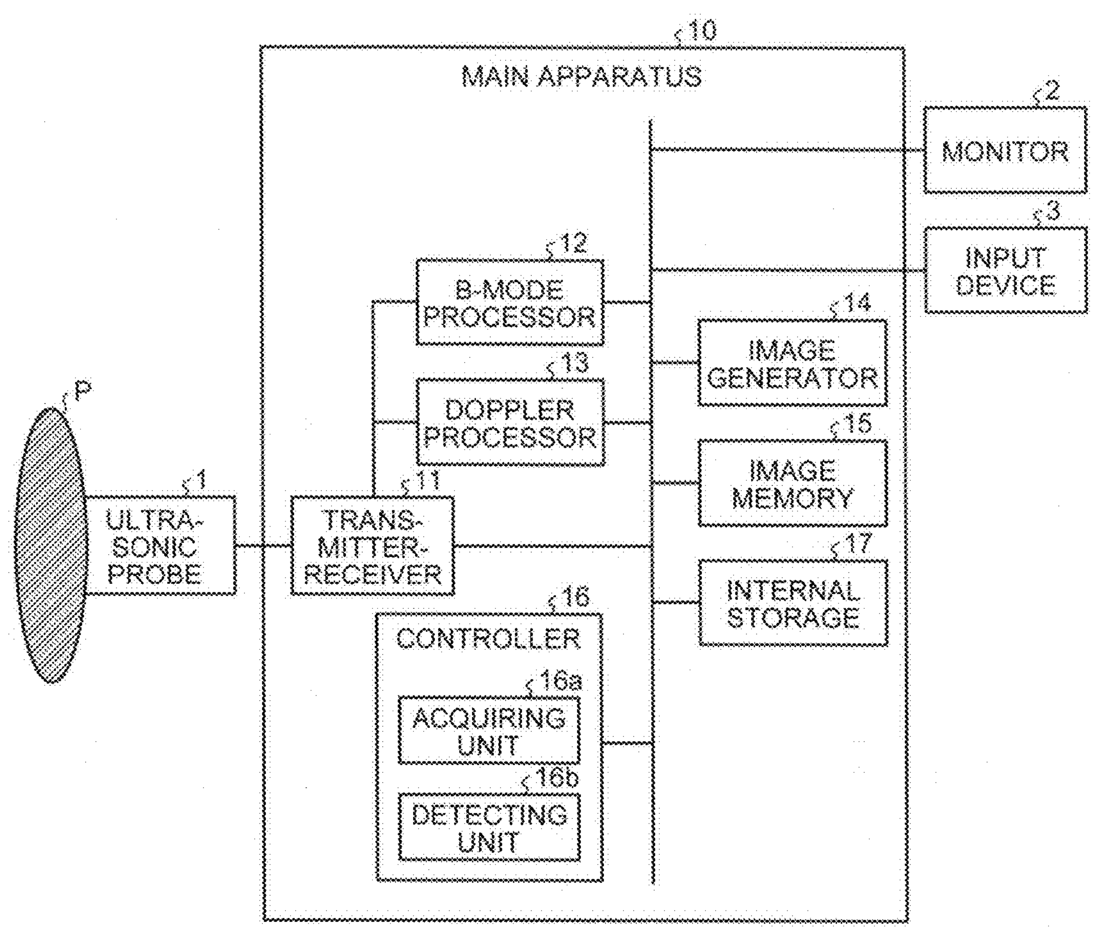
FIG. 1 is a block diagram illustrating an exemplary configuration of an ultrasonic diagnostic apparatus according to a first embodiment.

A configuration of an ultrasonic diagnostic apparatus according to a first embodiment will be explained. FIG. 1 is a block diagram illustrating an exemplary configuration of an ultrasonic diagnostic apparatus according to the first embodiment. As illustrated in FIG. 1, the ultrasonic diagnostic apparatus according to the first embodiment includes an ultrasonic probe 1, a monitor 2, an input device 3, and a main apparatus 10.

The ultrasonic probe 1 includes a plurality of piezoelectric transducer elements. The piezoelectric transducer elements generate ultrasonic waves based on driving signals supplied from a transmitter-receiver 11 provided in the main apparatus 10, which is to be explained later. The ultrasonic probe 1 also receives reflection waves from a subject P and converts the reflection waves into electrical signals. The ultrasonic probe 1 also includes matching layers provided on the piezoelectric transducer elements, and a backing material for preventing the ultrasonic waves from propagating backwardly from the piezoelectric transducer elements. The ultrasonic probe 1 is connected to the main apparatus 10 in a removable manner.

When an ultrasonic wave is transmitted from the ultrasonic probe 1 toward the subject P, the ultrasonic wave thus transmitted is reflected one after another on a discontinuous acoustic impedance surface in body tissue within the subject P, and received as reflection wave signals by the piezoelectric transducer elements in the ultrasonic probe 1. The amplitude of the reflection wave signals thus received depends on an acoustic impedance difference on the discontinuous surface on which the ultrasonic wave is reflected. When a transmitted ultrasonic wave pulse is reflected on the surface of a moving blood flow or of a cardiac wall, the frequency of the reflection wave signal thus received is shifted by the Doppler shift depending on the velocity component of the moving body with respect to the direction in which the ultrasonic wave is transmitted.

The ultrasonic probe 1 according to the first embodiment is an ultrasonic probe capable of scanning the subject P two-dimensionally, and of scanning the subject P three-dimensionally. Specifically, the ultrasonic probe 1 according to the first embodiment is a mechanical four-dimensional probe that scans the subject P two-dimensionally using a plurality of piezoelectric transducer elements that are arranged in a line, and scans the subject P three-dimensionally by swinging the piezoelectric transducer elements by a given angle (swinging angle). The ultrasonic probe 1 according to the first embodiment may also be a two-dimensional probe capable of performing three-dimensional ultrasonic scanning of the subject P by being provided with a plurality of piezoelectric transducer elements arranged in a matrix. A two-dimensional probe is also capable of scanning the subject P two-dimensionally by converging and transmitting ultrasounds.

The input device 3 includes a mouse, a keyboard, a button, a panel switch, a touch command screen, a foot switch, a track ball, and a joystick, for example. The input device 3 receives various setting requests from an operator of the ultrasonic diagnostic apparatus, and forwards the various setting requests thus received to the main apparatus 10.

The monitor 2 displays a graphical user interface (GUI) for allowing an operator of the ultrasonic diagnostic apparatus to enter various setting requests using the input device 3, and displays an ultrasound image generated by the main apparatus 10, for example.

The main apparatus 10 is an apparatus that generates ultrasound image data based on reflection wave signals received by the ultrasonic probe 1. Specifically, the main apparatus 10 according to the first embodiment is an apparatus cable of generating three-dimensional ultrasound image data based on three-dimensional reflection wave data received by the ultrasonic probe 1. Hereinafter, three-dimensional ultrasound image data is referred to as "volume data".

As illustrated in FIG. 1, the main apparatus 10 includes a transmitter-receiver 11, a B-mode processor 12, a Doppler processor 13, an image generator 14, an image memory 15, a controller 16, and an internal storage 17.

The transmitter-receiver 11 includes a pulse generator, a transmission delaying unit, and a pulser, and supplies a driving signal to the ultrasonic probe 1. The pulse generator generates a rate pulse used in generating ultrasonic waves to be transmitted, repeatedly at a given rate frequency. The transmission delaying unit adds a delay time corresponding to each of the piezoelectric transducer elements to each of the rate pulses generated by the pulse generator. Such a delay time is required for converging the ultrasonic waves generated by the ultrasonic probe 1 into a beam and determining transmission directivity. The pulser applies a driving signal (driving pulse) to the ultrasonic probe 1 at the timing of the rate pulse. In other words, by causing the transmission delaying unit to change the delay time to be added to each of the rate pulses, the direction in which the ultrasonic waves are transmitted from each of the piezoelectric transducer element surfaces is adjusted to a given direction.

The transmitter-receiver 11 has a function of changing a transmission frequency, a transmission driving voltage, and the like instantaneously before performing a certain scan sequence, based on an instruction of the controller 16 to be described later. In particular, the transmission driving voltage is changed by a linear amplifier type transmission circuit that is cable of switching its values instantaneously, or a mechanism for electrically switching a plurality of power units.

The transmitter-receiver 11 includes a preamplifier, an analog-to-digital (A/D) converter, a receiving delay circuit, and an adder. The transmitter-receiver 11 generates reflection wave data by applying various processes to the reflection wave signals received by the ultrasonic probe 1. The preamplifier amplifies the reflection wave signal on each channel. The A/D converter performs an A/D conversion of the reflection wave signal having amplified. The receiving delay circuit adds a delay time required for determining the reception directivity to the digital data. The adder performs an addition to the reflection wave signals processed by the receiving delay circuit, to generate the reflection wave data. Through the addition performed by the adder, a reflection component in the direction corresponding to the reception directivity of the reflection wave signals is emphasized, and a comprehensive beam transmitting and receiving ultrasound is formed with the reception directivity and the transmission directivity.

The transmitter-receiver 11 according to the first embodiment scans the subject P three-dimensionally by causing the ultrasonic probe 1 to transmit a three-dimensional ultrasonic beam toward the subject P. The transmitter-receiver 11 according to the first embodiment then generates three-dimensional reflection wave data from the three-dimensional reflection wave signals received by the ultrasonic probe 1.

The type of signals output from the transmitter-receiver 11 may be various types, e.g., a signal what is called a radio frequency (RF) signal containing phase information, or amplitude information acquired by an envelope detecting process.

The B-mode processor 12 receives the reflection wave data from the transmitter-receiver 11, and performs a logarithmic amplification, an envelope detection, and the like, to generate data in which a signal intensity is represented as a luminance (B-mode data).

The Doppler processor 13 frequency-analyzes the velocity information included in the reflection wave data received from the transmitter-receiver 11, extracts blood flow, tissues, and contrast agent echo components resulted from the Doppler shift, and generates data (Doppler data) that is moving body information such as velocity, variance, and power extracted for a plurality of points. A moving body in the embodiment may be a fluid such as blood flowing through a lumen.

The B-mode processor 12 and the Doppler processor 13 according to the first embodiment are capable of processing both of two-dimensional reflection wave data and three-dimensional reflection wave data. In other words, the B-mode processor 12 generates three-dimensional B-mode data from three-dimensional reflection wave data, and generates two-dimensional B-mode data from two-dimensional reflection wave data. The Doppler processor 13 generates two-dimensional Doppler data from two-dimensional reflection wave data, and generates three-dimensional Doppler data from three-dimensional reflection wave data. Three-dimensional B-mode data is data in which a luminance is assigned to a reflection intensity at a reflection source positioned at each of a plurality of points that are set to each scan line within the region scanned three-dimensionally. The three-dimensional Doppler data is data in which a luminance is assigned to a value representing blood flow information (velocity, variance, power) at each of the points set to each of the scan lines within the region scanned three-dimensionally.

The image generator 14 generates ultrasound image data from the data generated by the B-mode processor 12 and the data generated by the Doppler processor 13. The image generator 14 generates B-mode image data in which the intensity of a reflection wave is represented as a luminance from two-dimensional B-mode data generated by the B-mode processor 12. The B-mode image data is data representing tissue form (shapes of tissues) included in the ultrasonic-scanned region. The image generator 14 generates Doppler image data representing moving body information from the two-dimensional Doppler data generated by the Doppler processor 13. The Doppler image data is a velocity image, a variance image, or a power image, or a combination of these images. The Doppler image data is data representing moving body information related to a moving body that moves in the region ultrasonic-scanned.

Generally, the image generator 14 performs a conversion of rows of scan line signals in an ultrasonic scan into rows of scan line signals in a video format, typically one used for television (performs a scan conversion), for example, to generate ultrasound image data to be displayed. Specifically, the image generator 14 generates ultrasound image data to be displayed by performing a coordinate conversion in accordance with a way in which ultrasonic scanning is performed with the ultrasonic probe 1. The image generator 14 performs various types of image processing other than scan conversion, such as image processing in which an average luminance image is re-generated using a plurality of image frames applied with scan conversion (smoothing process), and image processing in which differential filtering is applied to an image (edge emphasizing process). The image generator 14 also synthesizes various character information of various parameters, scales, body marks, and the like to the ultrasound image data.

In other words, the B-mode data and the Doppler data are ultrasonic image data before the scan conversion processing. The data generated by the image generator 14 serves as the ultrasonic image data to be displayed applied with the scan conversion. The B-mode data and the Doppler data are also referred to as raw data. The three-dimensional B-mode data and the three-dimensional Doppler mode data are also referred to as volume data.

The image generator 14 also generates three-dimensional B-mode image data by performing a coordinate conversion of the three-dimensional B-mode data generated by the B-mode processor 12. The image generator 14 also generates three-dimensional Doppler image data by performing a coordinate conversion of the three-dimensional Doppler data generated by the Doppler processor 13. In other words, the image generator 14 generates "three-dimensional B-mode image data and three-dimensional Doppler image data" as "volume data as three-dimensional ultrasonic image data". In the explanation below, the three-dimensional B-mode image data is referred to as B-mode volume data, and three-dimensional Doppler image data is referred to as Doppler volume data. The B-mode volume data serves as tissue volume data representing the tissue form in the region (the scan region) that is three-dimensionally ultrasonic-scanned. The Doppler volume data serves as fluid volume data representing fluid information related to a fluid flowing through the region (the scan region) ultrasonic-scanned three-dimensionally.

The image generator 14 also applies a rendering process to the volume data to generate various types of two-dimensional image data to be displayed on the monitor 2. An example of the rendering process performed by the image generator 14 includes a process of performing multi-planer reconstruction (MPR) and generating an MPR image data from the volume data. Other examples of the rendering process performed by the image generator 14 includes a process of performing a "curved MPR" of the volume data, and a process of performing a "maximum intensity projection" of the volume data.

Another example of the rendering process performed by the image generator 14 includes a volume rendering (VR) process for generating two-dimensional image data reflected with three-dimensional information. For example, by performing a perspective projection as a volume rendering process, the image generator 14 can generate a virtual endoscopic (VE) image to be used in a fly-through view.

Explained now are approaches for displaying an image using Doppler data. The approaches for displaying an image using Doppler data are generally classified into color Doppler imaging (CDI) and power Doppler imaging (PDI). In the CDI, the image generator 14 generates color Doppler image data, in which a different hue is assigned depending on the direction and the velocity size of the blood flow. For example, the image generator 14 generates color Doppler image data in which a hue near red (from red to yellow) is assigned to a blood flow moving toward the ultrasonic probe 1 based on the velocity size of the blood flow, and a color near blue (from blue to blue green) is assigned to a blood flow moving away from the ultrasonic probe 1 based on the velocity size of the blood flow. In the CDI, there are cases in which the image generator 14 generates color Doppler image data in which velocity information and variance information are combined to indicate a velocity-variance relationship.

In the PDI, the image generator 14 generates power image data in which the hue, the lightness, or the saturation of a color near red, for example, is changed depending on the power representing the intensity of the Doppler signal.

When the CDI is applied to three-dimensional scanning, the image generator 14 generates color Doppler volume data from the three-dimensional Doppler data, as Doppler volume data. When the PDI is performed to three-dimensional scanning, the image generator 14 generates power volume data, in which the power representing the intensity of the Doppler signal is mapped to a three-dimensional space, from the three-dimensional Doppler data, as Doppler volume data. When the three-dimensional scanning is performed repeatedly along a time sequence, the image generator 14 is caused to generate the color Doppler volume data or the power volume data sequentially along the time sequence.

In the CDI, the detection precision of a fluid existing region depends on the direction of the blood flow and the relative positioning of the blood flow with respect to the ultrasonic probe 1. Specifically, in the CDI, the detection precision declines when a blood flow runs in a direction intersecting perpendicularly with the direction of the ultrasonic beam. By contrast, although the PDI does not allow detections of information related to the direction of or the velocity of a blood flow, the PDI enables a blood flow existing region to be detected independently from the direction of the blood flow or the relative positioning of the blood flow with respect to the ultrasonic probe 1.

Usually, Doppler image data is superimposed over B-mode image data before output to the monitor 2. In two-dimensional scanning or three-dimensional scanning, the transmitter-receiver 11 performs B-mode scanning and Doppler mode scanning in parallel. In B-mode scanning, an ultrasonic beam is transmitted and received once in a single scan line. In Doppler mode scanning, an ultrasonic beam is transmitted and received a plurality of times in a single scan line. The Doppler processor 13 generates Doppler data by performing a moving target indicator (MTI) filtering, an auto correlation calculation, and a velocity/variance/power estimation, for a plurality of pieces of reflection wave data acquired from the same scan line.

The image memory 15 illustrated in FIG. 1 is a memory storing therein image data to be displayed generated by the image generator 14. The image memory 15 can also store therein data generated by the B-mode processor 12 or the Doppler processor 13. The B-mode data or the Doppler data is stored in the image memory 15 so that an operator can refer to the data after making a diagnosis, for example, and comes to serve as ultrasonic image data to be displayed via the image generator 14.

The internal storage 17 stores therein various types of data such as control programs for transmitting and receiving ultrasound, for performing image processing, and for performing displaying processes, diagnostic information (e.g., a patient identification (ID) and observations by a physician), diagnostic protocols, and various body marks. The internal storage 17 is also used for storing image data stored in the image memory 15, as required. The data stored in the internal storage 17 may be forwarded to an external device via an interface not illustrated.

The controller 16 controls the entire processes performed by the ultrasonic diagnostic apparatus. Specifically, the controller 16 controls the processes performed by the transmitter-receiver 11, the B-mode processor 12, the Doppler processor 13, and the image generator 14, based on various setting requests entered by an operator via the input device 3, and various control programs and various types of data read from the internal storage 17. The controller 16 also controls to display ultrasonic image data to be displayed stored in the image memory 15 or the internal storage 17 on the monitor 2. As illustrated in FIG. 1, the controller 16 according to the first embodiment includes an acquiring unit **16*a* and a detecting unit 16*b*. The acquiring unit 16*a* and the detecting unit 16*b*** will be described later in detail.

The entire configuration of the ultrasonic diagnostic apparatus according to the first embodiment is explained so far. With such a configuration, the ultrasonic diagnostic apparatus according to the first embodiment performs three-dimensional scanning of a region including a lumen filled with a fluid, and generates B-mode volume data. Examples of a lumen filled with a fluid include a blood vessel, a bile duct, and a lymph gland. The ultrasonic diagnostic apparatus according to the first embodiment then generates various types of image data for enabling the inner wall of the lumen to be observed using the B-mode volume data. For example, the ultrasonic diagnostic apparatus according to the first embodiment sequentially generates VE images from different viewpoint positions, by shifting the viewpoint position along the center line (central line) of the lumen, and displays the VE images so that a fly-through view of the lumen is provided. When a fly-through view is provided, an operator can observe the lumen from the inner side, without inserting an endoscope in the subject P, or without inserting a transducer element catheter into a blood vessel of the subject P in an intravascular ultrasound (IVUS). When a fly-through view of the lumen is to be provided, a clipping region, which a region is to be rendered, would be the inner wall of the lumen.

Because contours between structures tends to blur more in a B-mode image than in other medical images such as an X-ray CT image or an MRI image, it has been difficult to detect the inner cavity region of a lumen in B-mode volume data by means of automatic processing using a computer program, unless the lumen has a certain diameter or larger. In particular, because a blood vessel moves vigorously due to pulsation, contours along a blood vessel tend to blur even more. Therefore, it is currently impossible to detect a clipping region unless the lumen has a certain diameter or larger. Due to such a reason, a fly-through view in a conventional ultrasonic diagnostic apparatus has been limited to tubular structures having a certain diameter or larger, and it has been difficult to apply such an ultrasonic diagnostic apparatus to thin tubular structures.

In order to enable the inner cavity region of a lumen to be detected easily, the ultrasonic diagnostic apparatus according to the first embodiment causes the acquiring unit **16*a* and the detecting unit 16*b*** to perform the processes explained below.

The acquiring unit **16*a* acquires fluid volume data representing fluid information related to a fluid flowing through a region (a scan region) that is three-dimensionally ultrasonic-scanned. The detecting unit 16*b* then uses the fluid information to detect a region that is a fluid existing region in the scan region, and uses the region thus detected to detect the inner cavity region of a lumen in the volume data which is to be applied with the image processing. In the first embodiment, the acquiring unit 16*a* also acquires tissue volume data representing the tissue form in the scan region as the volume data to be applied with the image processing. Specifically, in the first embodiment, the acquiring unit 16*a* acquires tissue volume data generated by three-dimensional ultrasonic-scanning of the scan region as the tissue volume data. In other words, the acquiring unit 16*a* according to the first embodiment acquires tissue volume data representing the tissue form in the scan region that is three-dimensionally ultrasonic-scanned, and fluid volume data representing fluid information related to a fluid flowing through the scan region that is three-dimensionally ultrasonic-scanned. The detecting unit 16**_b_ according to the first embodiment then uses the fluid information in the fluid volume data to detect a region that is a fluid existing region in the scan region, and uses the region thus detected to detect the inner cavity region of a lumen included in the tissue volume data.

In other words, in the first embodiment, B-mode scanning and Doppler mode scanning are performed in order to enable the inner wall of a lumen to be observed. Specifically, in the first embodiment, B-mode scanning and Doppler mode scanning are performed across the same region. More specifically, in the first embodiment, the operator holds the ultrasonic probe 1 against a position of the subject P that allows a region including the lumen, which is the target of the observation, to be three-dimensionally scanned. The operator then gives an instruction for performing three-dimensional B-mode scanning and three-dimensional Doppler mode scanning in parallel. In response, the transmitter-receiver 11 generates three-dimensional B-mode reflection wave data and three-dimensional Doppler mode reflection wave data. The B-mode processor 12 then generates the three-dimensional B-mode data from the three-dimensional B-mode reflection wave data, and the Doppler processor 13 generates three-dimensional Doppler data from the three-dimensional Doppler mode reflection wave data. The image generator 14 then generates B-mode volume data from the three-dimensional B-mode data, and generates Doppler volume data from the three-dimensional Doppler data.

The PDI enables a fluid existing region, e.g., a blood flow existing region, to be detected at a higher precision than the CDI, as mentioned earlier. Therefore, an operator gives an instruction to collect power volume data as the Doppler volume data. In other words, the image generator 14 is caused to generate power volume data. In the first embodiment, color Doppler volume data may alternatively be collected, when it can be determined that the detecting precision of a blood flow existing region would not decline, based on the direction in which a lumen runs, for example.

In the first embodiment, three-dimensional scanning is performed once to generate each of the B-mode volume data and the power volume data in the same temporal phase. The acquiring unit 16_a_ acquires the B-mode volume data and the power volume data from the same temporal phase stored in the image memory 15, and transmits the B-mode volume data and the power volume data from the same temporal phase to the detecting unit 16_b_.

In the first embodiment, three-dimensional scanning may alternatively be performed a plurality of times, to generate a plurality of pieces of each of the B-mode volume data and the power volume data along a time sequence. In such a case, an operator designates a piece of B-mode volume data suitable for observations by examining each of the MPR images of the B-mode volume data thus collected, for example. The acquiring unit 16_a_ then acquires the B-mode volume data designated by the operator and the power volume data collected at the same time as the B-mode volume data, and transmits the volume data to the detecting unit 16_b_.

The detecting unit 16_b_ then detects a fluid existing region using the fluid information of the fluid volume data, and detects the inner cavity region of a lumen included in the tissue volume data using the region thus detected, as described earlier. In the first embodiment, the detecting unit 16_b_ detects a fluid existing region using the position information of voxels, each of which is assigned with a luminance because a power is detected, in the power volume data.

In other words, the power volume data is data in which voxels at the positions corresponding to a fluid are assigned with a value representing a color corresponding to a power, which is one type of fluid information. The detecting unit 16_b_ can detect a fluid existing region from the power volume data. The B-mode volume data and the power volume data are generated using the same coordinate system. In other words, "coordinates of a fluid existing region" detected from the power volume data are the same as "coordinates of a fluid existing region" in the B-mode volume data. A fluid existing region corresponds to a region in which a fluid flowing through the inner cavity of a lumen exists, and corresponds to the inner cavity region of the lumen included in the B-mode volume data. A process performed by the detecting unit 16_b_ will now be explained with reference to FIGS. 2 to 5. FIGS. 2 to 5 are schematics for explaining the detecting unit according to the first embodiment.

Figure 2:
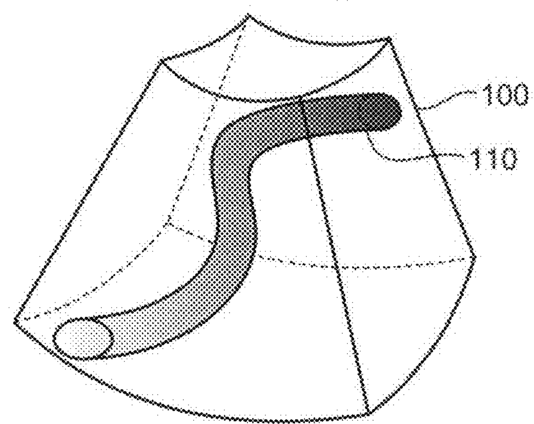
FIG. 2, FIG. 3, FIG. 4, and FIG. 5 are schematics for explaining the detecting unit according to the first embodiment.

The detecting unit 16_b_ detects a fluid region 110 that is a "fluid existing region" in power volume data 100, which is illustrated in FIG. 2. Specifically, the detecting unit 16_b_ detects the coordinates of voxels delineating the contours of the fluid section 110. A specific example of the process performed by the detecting unit 16_b_ will now be explained with reference to FIGS. 3 and 4.

Figure 3:
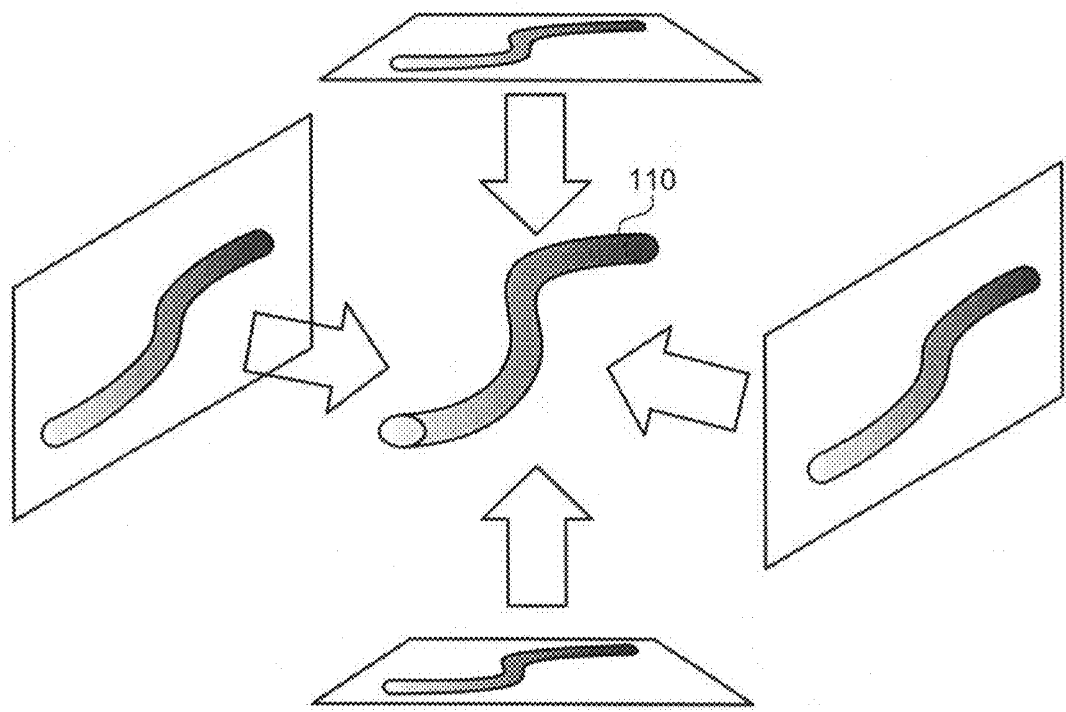

In the process illustrated in FIG. 3, the detecting unit 16_b_ detects the coordinates of the surface of the fluid section 110 using surface rendering, which is a rendering technique. Surface rendering is a rendering technique projecting only the voxels representing the first volume that the line of sight encounters, assuming that the volume data is viewed from a direction of a viewpoint position. In other words, the position of the surface of an object in a volume can be acquired by performing surface rendering from a plurality of viewpoint positions.

The detecting unit 16_b_ sets a plurality of viewpoint positions to the power volume data 100, and sets a line of sight in a direction travelling toward the center or the gravity center of the power volume data 100 from each of the viewpoint positions. The detecting unit 16_b_ then detects the coordinates of the surface of the fluid section 110 based on the results of surface rendering performed from each of the viewpoint positions, as illustrated in FIG. 3. The surface rendering process applied to the power volume data 100 may be performed by the detecting unit 16_b_, or may be performed by the image generator 14 under the control of the detecting unit 16_b_.

Figure 4:
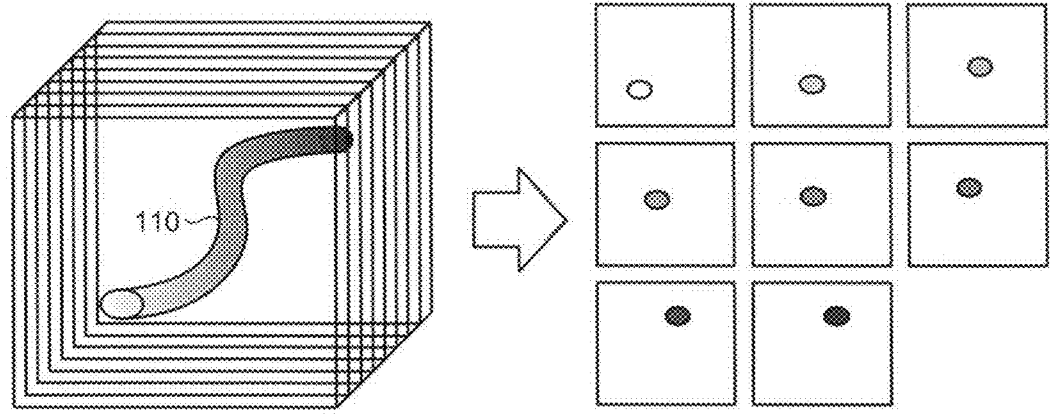

In the process illustrated in FIG. 4, the detecting unit 16_b_ detects the coordinates of the surface of the fluid section 110 using MPR, which is another rendering technique. In other words, the detecting unit 16_b_ sets a plurality of cross sections extending in parallel to the power volume data 100. The contour along the fluid section 110 is represented in each of a plurality of MPR images reconstructed from the power volume data 100 based on the cross sections thus set, as illustrated in FIG. 4. The detecting unit 16_b_ then detects the coordinates of the surface of the fluid section 110 by detecting the contour of the fluid section 110 in each of the MPR images, and connecting the contours detected from the respective MPR images. The MPR process applied to the power volume data 100 may be performed by the detecting unit 16_b_, or performed by the image generator 14 under the control of the detecting unit 16_b_.

Various techniques such as region growing other than those explained with reference to FIG. 3 or FIG. 4 may also be used as a process of detecting the fluid section 110.

Figure 5:
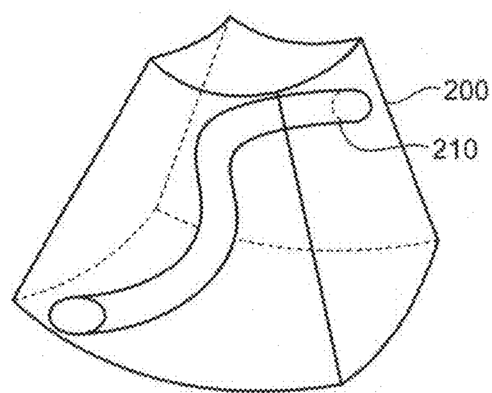

The detecting unit 16*b* detects the coordinates of the surface (contour) of the fluid section 110 thus detected as the coordinates of the surface (contour) of an inner cavity region 210 in B-mode volume data 200 received from the acquiring unit 16*a*, as illustrated in FIG. 5. The surface of the inner cavity region 210 represents the inner wall of the inner cavity region 210. The detecting unit 16*b* then establishes the surface of the inner cavity region 210 as a clipping region. To reduce noise, for example, the detecting unit 16*b* may apply a post-process such as a smoothing filtering to the surface of the fluid section 110 thus detected or the surface of the inner cavity region 210.

The image generator 14 then generates image data to be displayed on the monitor 2 from the tissue volume data (B-mode volume data), using the surface of the inner cavity region detected by the detecting unit 16*b* as a target of the process. FIGS. 6, 7A, 7B, and 7C are schematics for explaining the image generator according to the first embodiment.

Figure 6:
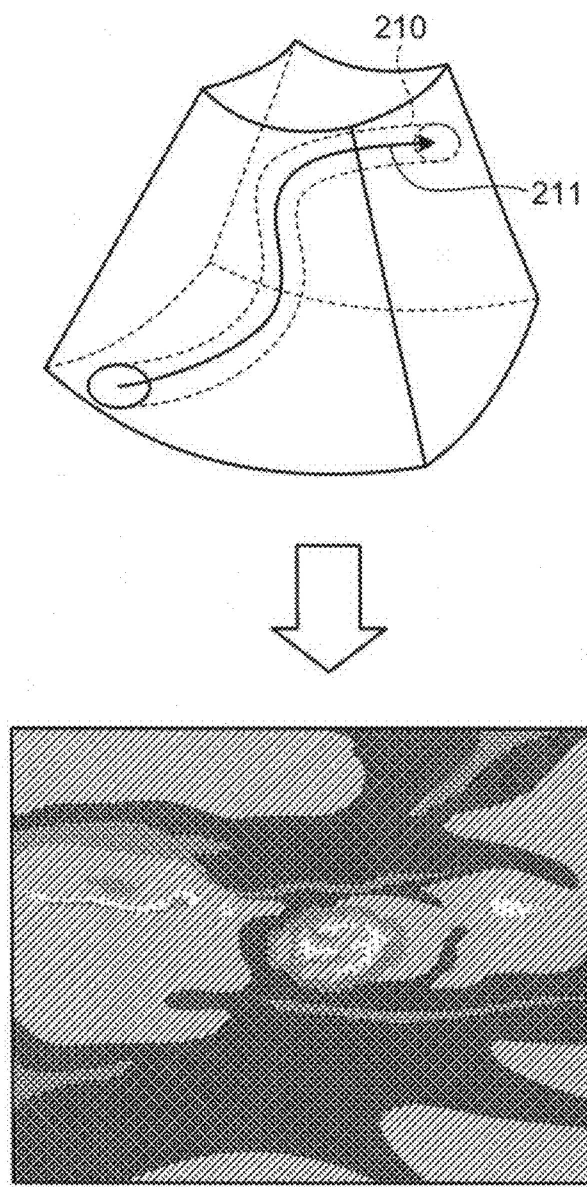
FIG. 6, FIG. 7A, FIG. 7B, and FIG. 7C are schematics for explaining the image generator according to the first embodiment.

The image generator 14 generates a projected image that is a projection of the tissue volume data from the viewpoint positions set inside of the lumen based on the inner cavity region detected by the detecting unit 16*b*, as the image data to be displayed on the monitor 2. Specifically, the image generator 14 extracts the center line of the lumen from the data in which the inner cavity region is removed from the tissue volume data, and generates a plurality of projected images by shifting the viewpoint position along the center line, as an image data group to be displayed as dynamic images on the monitor 2. For example, the image generator 14 extracts a center line 211 of the inner cavity region 210, as illustrated in FIG. 6. The image generator 14 then generates VE images from the clipping region (the contour of the inner cavity region 210), using each of the viewpoint positions set along the center line 211, as illustrated in FIG. 6. The image generator 14 sequentially generates the VE images to be used for a fly-through view, by shifting the viewpoint position along the center line 211.

Figure 7A:
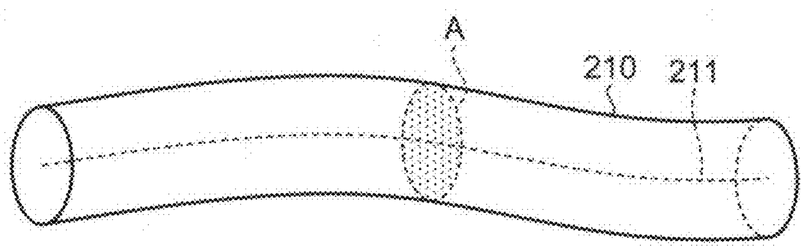
Figure 7B:
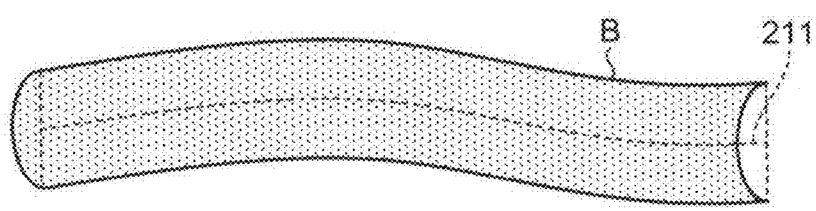

Alternatively, the image generator 14 may generate MPR image data A representing the inner cavity region 210 cut across a cross section perpendicularly intersecting with the center line 211, as illustrated in FIG. 7A, for example. Alternatively, the image generator 14 may generate curved MPR image data B representing the inner cavity region 210 cut across the cross section including the entire center line 211 (curved surface), as illustrated in FIG. 7B, for example.

Figure 7C:
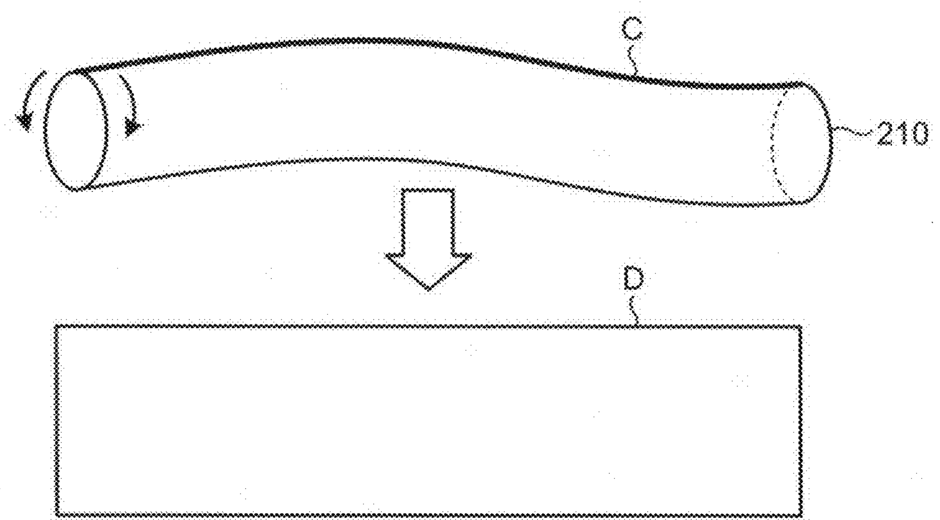

Alternatively, the image generator 14 may generate expanded image data D representing the inner cavity region 210 cut open along a curve C at which a cross section including the entire center line 211 intersects with a contour line of the inner cavity region 210, as illustrated in FIG. 7C, for example. By referring to the image data illustrated in FIGS. 7A, 7B, and 7C on the monitor 2, an operator can observe the shapes of the inner wall of the inner cavity region 210.

Figure 8:
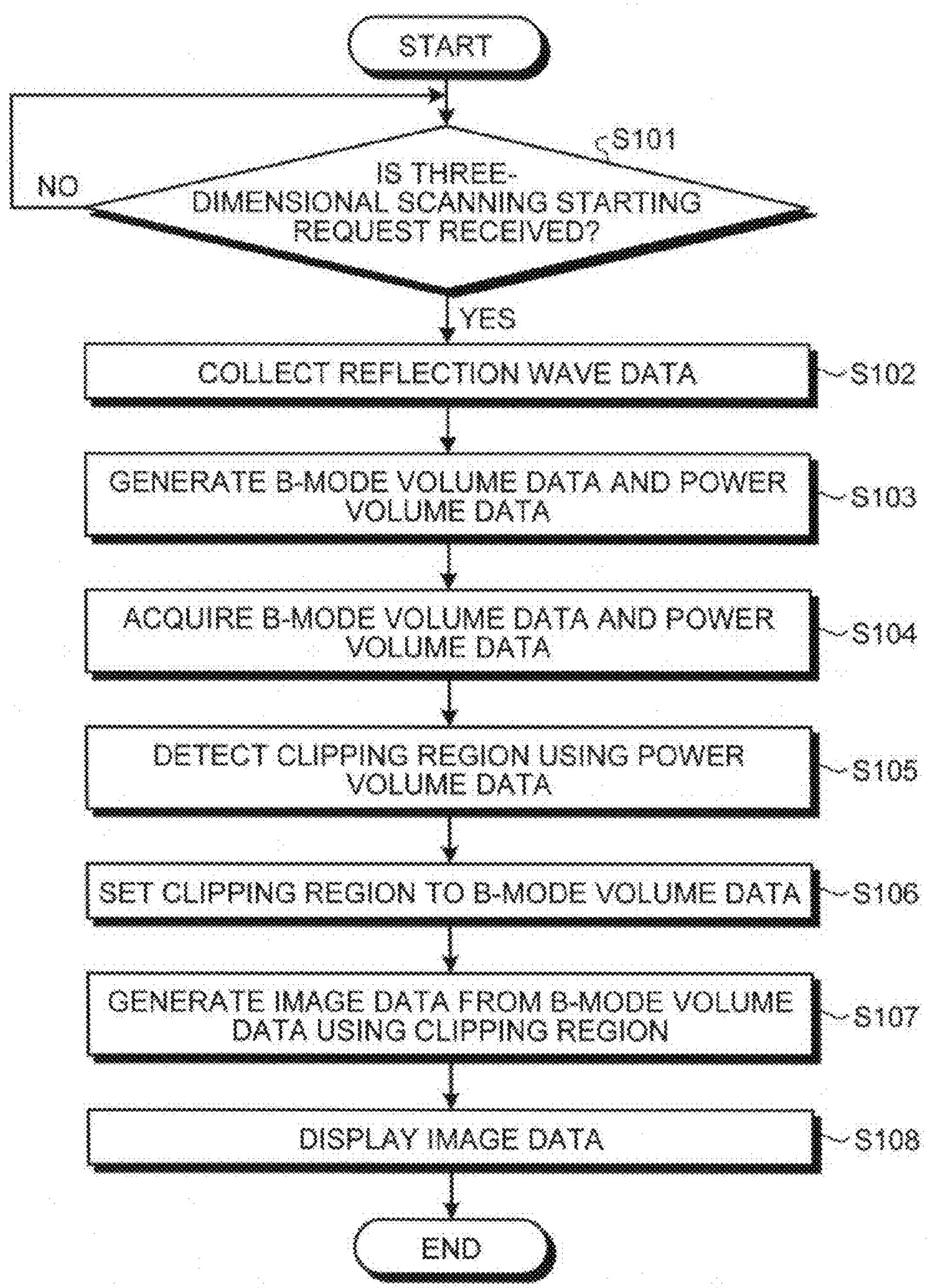
FIG. 8 is a flowchart for explaining an exemplary process performed by the ultrasonic diagnostic apparatus according to the first embodiment.

A process performed by the ultrasonic diagnostic apparatus according to the first embodiment will now be explained with reference to FIG. 8. FIG. 8 is a flowchart for explaining an exemplary process performed by the ultrasonic diagnostic apparatus according to the first embodiment.

As illustrated in FIG. 8, the ultrasonic diagnostic apparatus according to the first embodiment determines if a three-dimensional scanning starting request is received (Step S101). If any three-dimensional scanning starting request is not received (No at Step S101), the ultrasonic diagnostic apparatus waits until a three-dimensional scanning starting request is received.

If a three-dimensional scanning starting request is received (Yes at Step S101), the ultrasonic probe 1 performs three-dimensional ultrasonic scanning, and the transmitter-receiver 11 collects the three-dimensional reflection wave data under the control of the controller 16 (Step S102). The ultrasonic probe 1 performs the three-dimensional B-mode scanning and the three-dimensional Doppler mode scanning in parallel. The transmitter-receiver 11 then generates the three-dimensional B-mode reflection wave data and the three-dimensional Doppler mode reflection wave data.

The image generator 14 then generates the B-mode volume data and power volume data (Step S103). The acquiring unit 16*a* then acquires the B-mode volume data and the power volume data (Step S104), and forwards the data to the detecting unit 16*b*.

The detecting unit 16*b* then detects a clipping region representing the surface of the inner cavity region of a lumen using the power volume data (Step S105), and sets the clipping region to the B-mode volume data (Step S106).

The image generator 14 then generates the image data to be displayed from the B-mode volume data using the clipping region (Step S107). The monitor 2 then displays the image data under the control of the controller 16 (Step S108), and the process is ended.

As described above, in the first embodiment, the process of detecting a clipping region, which is required to enable observations of the inner wall of a lumen, from the B-mode volume data is performed using the Doppler volume data of the same region as that of the B-mode volume data. In other words, in the first embodiment, a clipping region can be detected highly precisely without depending on the diameter of the lumen, as long as the lumen is located at a position where a fluid can be detected in the Doppler mode. Therefore, in the first embodiment, the inner cavity region of a lumen can be easily detected.

Furthermore, in the first embodiment, because a clipping region can be detected highly precisely without depending on the diameter of a lumen, the applicable scope of lumens from which hemadostenosis is searched with a fly-through view or the like can be expanded. Furthermore, although use of a contrast agent is available as an option for detecting a clipping region, because the first embodiment enables a clipping to be detected highly precisely without using any contrast agent, burdens on the subject P can be reduced.

Second Embodiment

Figure 9:
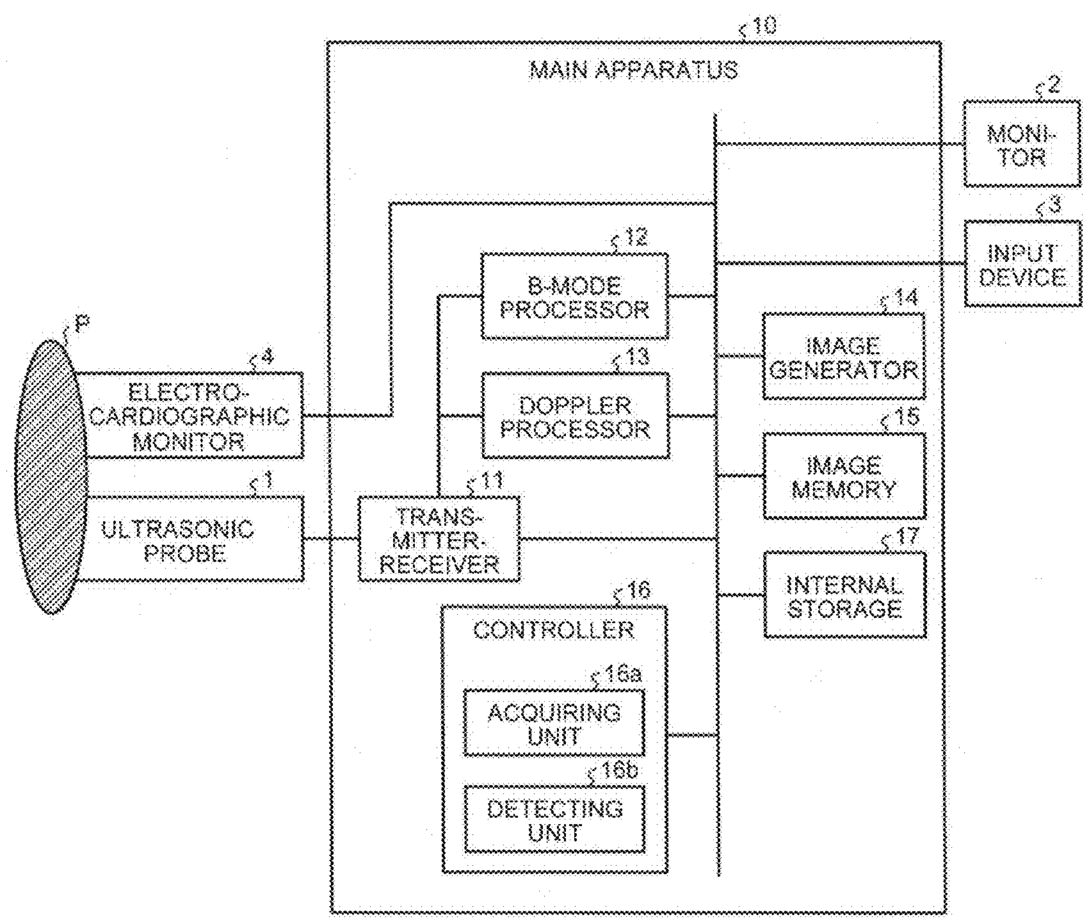
FIG. 9 is a block diagram illustrating an exemplary configuration of an ultrasonic diagnostic apparatus according to a second embodiment.
Figure 10:
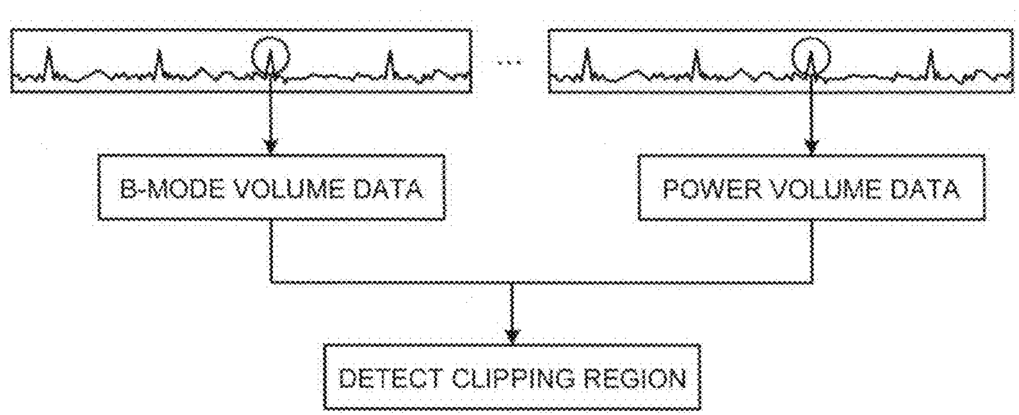
FIG. 10 is a schematic for explaining an acquiring unit and a detecting unit according to the second embodiment.

Explained in a second embodiment with reference to FIGS. 9 and 10 is an example in which the tissue volume data and the fluid volume data are collected separately at different times. FIG. 9 is a block diagram illustrating an exemplary configuration of an ultrasonic diagnostic apparatus according to the second embodiment. FIG. 10 is a schematic for explaining an acquiring unit and a detecting unit according to the second embodiment.

The amount of calculation required in collecting the Doppler mode data is larger than that required in collecting the B-mode data. Therefore, in order to improve the temporal resolution and the spatial resolution of the Doppler mode image data, it is preferable to collect the B-mode data and the Doppler mode data separately, while the position of the ultrasonic probe 1 is kept fixed. However, in order to detect a clipping region in the B-mode volume data using the Doppler volume data collected at different times, these two pieces of volume data which are the targets of the detection need to be the data collected from the same temporal phase.

As illustrated in FIG. 9, the ultrasonic diagnostic apparatus according to the second embodiment is different in that an electrocardiographic monitor 4 is connected to the main apparatus 10 having the same configuration as the ultrasonic diagnostic apparatus according to the first embodiment illustrated in FIG. 1. The electrocardiographic monitor 4 acquires an electrocardiogram (ECG) of a subject P from which the data is collected (the subject P who is three-dimensionally scanned) as a biological signal of the subject P. The electrocardiographic monitor 4 transmits the ECG thus acquired to the main apparatus 10.

The acquiring unit 16*a* according to the second embodiment acquires the tissue volume data and the fluid volume from the same temporal phase using the biological signal of the subject P from which the data is collected (the subject P who is three-dimensionally scanned), when the tissue volume data and the fluid volume data are collected sequentially and separately at different times. The detecting unit 16*b* then detects the inner cavity region through the process explained in the first embodiment, using the tissue volume data and the fluid volume data belonging to the same cardiac phase.

An example of the process performed in the second embodiment will now be explained. In the second embodiment, the ultrasonic probe 1 performs three-dimensional B-mode scanning to collect a plurality of volumes of B-mode volume data, which is the tissue volume data, along a time sequence. In the second embodiment, the ultrasonic probe 1 performs three-dimensional Doppler mode scanning to collect a plurality of volumes of power volume data, which is the fluid volume data, along the time sequence. The transmitter-receiver 11 causes the ultrasonic probe 1 to perform the three-dimensional Doppler mode scanning using a scanning sequence resulting in the most appropriate temporal resolution and spatial resolution.

The image generator 14 then stores the volume data and the time at which the ultrasonic scanning for generating the volume data is performed in the image memory 15, in a manner associated with the ECG received from the electrocardiographic monitor 4. The acquiring unit 16*a* can acquire the cardiac temporal phase in which the ultrasonic scanning for generating the volume data is performed, by referring to the data stored in the image memory 15.

The acquiring unit 16*a* then acquires the B-mode volume data and the power volume data from the same cardiac temporal phase from the image memory 15. In the example illustrated in FIG. 10, the acquiring unit 16*a* acquires the B-mode volume data and the power volume data corresponding to an R wave. The temporal phase to which the data to be acquired by the acquiring unit 16*a* belongs may be specified by an operator, or provided as a factory default.

The detecting unit 16*b* then detects a clipping region (the surface of an inner cavity region) from the power volume data corresponding to the R wave, as illustrated in FIG. 10, and sets the clipping region thus detected to the B-mode volume data corresponding to the R wave. The image generator 14 then generates image data to be displayed using the clipping region set in the B-mode volume data corresponding to the R wave.

In the second embodiment, the three-dimensional B-mode scanning may be performed subsequent to the three-dimensional Doppler mode scanning. Furthermore, in the second embodiment, color Doppler volume data may be collected as the fluid volume data, in the same manner as mentioned in the first embodiment.

Furthermore, in the second embodiment, alternatively, the tissue volume data and the fluid volume data from the same temporal phase may be acquired from a plurality of temporal phases (e.g., R wave and P wave), and a clipping region may be detected in each of the temporal phases. Furthermore, in the second embodiment, as a biological signal for identifying a cardiac phase, a phonocardiogram (PCG) or a respiration signal may also be used, instead of an ECG.

A process performed by the ultrasonic diagnostic apparatus according to the second embodiment will now be explained with reference to FIG. 11. FIG. 11 is a flowchart for explaining an exemplary process performed by the ultrasonic diagnostic apparatus according to the second embodiment.

As illustrated in FIG. 11, the ultrasonic diagnostic apparatus according to the second embodiment determines if a B-mode scanning starting request is received (Step S201). If any B-mode scanning starting request is not received (No at Step S201), the ultrasonic diagnostic apparatus waits until a B-mode scanning starting request is received.

If a B-mode scanning starting request is received (Yes at Step S201), the ultrasonic probe 1 starts three-dimensional ultrasonic scanning following a B-mode scanning sequence under the control of the controller 16, and the controller 16 starts collecting the ECG. The transmitter-receiver 11 collects the three-dimensional reflection wave data (Step S202), and generates three-dimensional B-mode reflection wave data.

The image generator 14 then generates the B-mode volume data (Step S203), and the controller 16 determines if a Doppler mode scanning starting request is received (Step S204). If any Doppler mode scanning starting request is not received (No at Step S204), the ultrasonic diagnostic apparatus returns to Step S202, and continues collecting the three-dimensional B-mode reflection wave data.

If a Doppler mode scanning starting request is received (Yes at Step S204), the ultrasonic probe 1 starts three-dimensional ultrasonic scanning following a Doppler mode scanning sequence under the control of the controller 16, and the transmitter-receiver 11 collects the three-dimensional reflection wave data (Step S205). The transmitter-receiver 11 then generates the three-dimensional Doppler mode reflection wave data.

The image generator 14 then generates the power volume data (Step S206), and the controller 16 determines if a clipping region setting request is received (Step S207). If any clipping region setting request is not received (No at Step S207), the ultrasonic diagnostic apparatus returns to Step S205, and continue collecting the three-dimensional Doppler mode reflection wave data.

If a clipping region setting request is received (Yes at Step S207), the acquiring unit 16*a* acquires the B-mode volume data and the power volume data from the same temporal phase (Step S208). The detecting unit 16*b* then detects a clipping region using the power volume data (Step S209), and sets the clipping region to the B-mode volume data (Step S210).

The image generator 14 generates image data to be displayed from the B-mode volume data using the clipping region (Step S211). The monitor 2 then displays the image data under the control of the controller 16 (Step S212), and the process is ended.

As described above, in the second embodiment, a clipping region can be detected from B-mode volume data belonging to a given temporal phase by using Doppler volume data belonging to the given temporal phase and collected separately following an optimized scanning sequence. Therefore, in the second embodiment, a clipping region can be detected more precisely.

Third Embodiment

Explained in a third embodiment is an example in which a lumen shape analysis is performed in more detail using a clipping region detected in the first embodiment or the second embodiment.

In the third embodiment, the acquiring unit 16*a* acquires the tissue volume data and the fluid volume data using the method disclosed in the first embodiment or in the second embodiment. In the third embodiment, the detecting unit 16*b* detects a clipping region from the tissue volume data using the method disclosed in the first embodiment. The detecting unit 16*b* according to the third embodiment then performs the process described below using the center line extracted in the fly-through view mentioned above.

Figure 12:
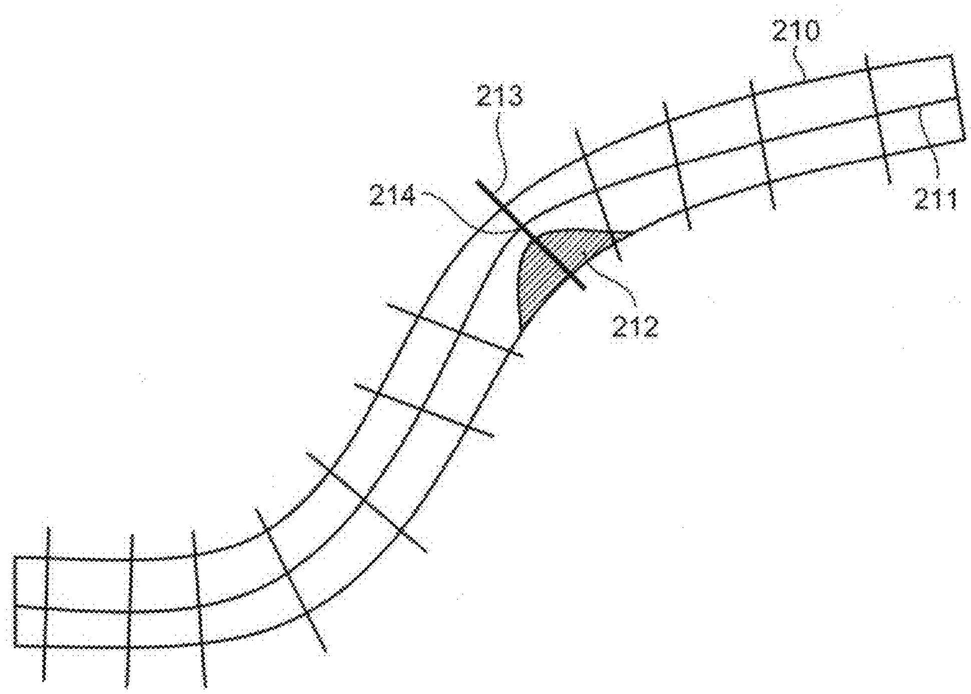
FIG. 12 is a schematic for explaining a detecting unit according to a third embodiment.

The detecting unit 16*b* calculates the area of each of a plurality of cross sections of the inner cavity region, each section perpendicularly intersecting with the center line of the inner cavity region. The detecting unit 16*b* then detects a cross section having an area deviating from those calculated for nearby cross sections as an abnormal cross section. FIG. 12 is a schematic for explaining the detecting unit according to the third embodiment.

For example, the detecting unit 16*b* establishes a plurality of cross sections perpendicularly intersecting with the center line 211 of the inner cavity region 210 extracted by the image generator 14, as illustrated in FIG. 12. For example, the detecting unit 16*b* establishes a plurality of cross sections at a constant interval (e.g., 1 millimeter) along the center line 211. The interval may be specified by an operator, or may be provided as a factory default.

The detecting unit 16*b* then calculates the area surrounded by an intersecting line between each of the cross sections and the contour line of the inner cavity region 210 (clipping region). Assuming that the inner cavity region 210 is an inner cavity region of a blood vessel, the area calculated by the detecting unit 16*b* for each of the cross sections is the cross-sectional area of the inner wall of the blood vessel.

For example, the cross-sectional area calculated for a cross section with a stenosis is much smaller than the cross-sectional areas calculated for the nearby cross sections. By contrast, the cross-sectional area calculated for a cross section including a region with an aneurysm in a blood vessel such as an arterial aneurysm would be larger than the cross-sectional areas calculated for nearby cross sections.

Therefore, the detecting unit 16*b* detects a cross section with the smallest area or a cross section with the largest area as an abnormal cross section, for example. Alternatively, in order to improve the detection precision, the detecting unit 16*b* may calculate the amount of change in the cross-sectional areas along the center line 211, and detect a cross section with the largest change as an abnormal cross section, for example.

Alternatively, in order to improve the detection precision, the detecting unit 16*b* may use the fluid information in the fluid volume data as a parameter for the detection. When color Doppler volume data collected as the fluid volume data, the detecting unit 16*b* may extract the flow rate extracted from the intersecting line on each of the cross sections. The flow rate tends to increase in a region with a stenosis, because the cross-sectional area of the blood vessel is small in such a region. Therefore, the detecting unit 16*b* detects a cross section with the highest flow rate, among those having an area smaller than a given threshold, as an abnormal cross section, for example.

By performing the process described above, the detecting unit 16*b* detects an abnormal cross section 213 illustrated in FIG. 12, for example. The abnormal cross section 213 is a cross section passing a region with the largest portion of a stenosis region 212, as illustrated in FIG. 12.

Figure 15:
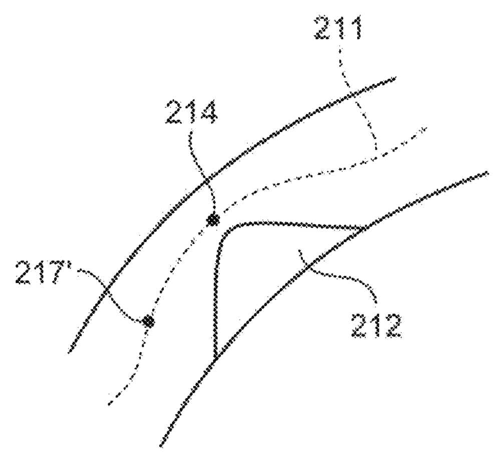

The image generator 14 according to the third embodiment then generates image data to be displayed on the monitor 2 from the tissue volume data (B-mode volume data), which is the volume data to be applied with the image processing, using the abnormal cross section. In other words, the image generator 14 uses the abnormal cross section as a clipping plane to be applied with a rendering process. The image data generated by the image generator 14 according to the third embodiment will now be explained with reference to FIGS. 13 to 15. FIGS. 13 to 15 are schematics for explaining the image generator according to the third embodiment.

In the example illustrated in FIG. 13, the image generator 14 dissects the B-mode volume data 200 across the abnormal cross section 213 into two regions, and generates B-mode volume data 201 in which one of the regions is removed. A point 214 illustrated in FIG. 13 is an intersecting point between the abnormal cross section 213 and the center line 211. The image generator 14 then generates the image data using the B-mode volume data 201.

For example, the image generator 14 generates an MPR image data 215 of the abnormal cross section 213 positioned on the surface of the B-mode volume data 201, as illustrated in FIG. 13. The outer wall as well as the inner wall of the blood vessel on the abnormal cross section 213 are represented in the MPR image data 215, as illustrated in FIG. 13. By observing the MPR image data 215, an operator can recognize the shape of the most bulged portion of the stenosis region 212.

The image generator 14 may also generate a VR image or an MIP image using the B-mode volume data 201. Furthermore, the image generator 14 may generate an MIP image with a thickness using the B-mode volume data 201 of a region interposed between the abnormal cross section 213 and another cross section extending in parallel with the abnormal cross section 213.

Illustrated in FIG. 14 is an example in which a clipping plane is changed by rotating the abnormal cross section 213, which is the clipping plane, freely about the point 214. For example, an operator sets a cross section 216 which is the abnormal cross section 213 rotated as a clipping plane, as illustrated in FIG. 14, by operating a trackball. An example of the cross section 216 is a cross section perpendicularly intersecting with the abnormal cross section 213.

The image generator 14 dissects the B-mode volume data 200 into two regions across the cross section 216, and generates B-mode volume data 202 in which one of the regions is removed, as illustrated in FIG. 14. The image generator 14 then generates image data using the B-mode volume data 202.

For example, the image generator 14 generates an MPR image data 217 of the cross section 216 positioned on the surface of the B-mode volume data 202, as illustrated in FIG. 14. Represented in the MPR image data 217 are the inner wall as well as the outer wall of a blood vessel approximately following the direction in which the blood vessel runs in the cross section 216, as illustrated in FIG. 14. By observing the MPR image data 217, an operator can recognize the shape of the stenosis region 212 along the direction in which the blood vessel runs.

The image generator 14 may generate a VR image or an MIP image using the B-mode volume data 202. Furthermore, the image generator 14 may generate an MIP image with a thickness using the B-mode volume data 202 of a region interposed between the cross section 216 and another cross section extending in parallel with the cross section 216.

Illustrated in FIG. 15 is an example in which the starting point of a fly-through view is automatically set using the point 214 identified using the abnormal cross section 213 detected by the detecting unit 16*b*. The detecting unit 16*b* sets a point 217' along the center line 211 positioned near the point 214 as a viewpoint position at which a fly-through view is started, as illustrated in FIG. 15. For example, the detecting unit 16*b* sets a point distant from the point 214 by 3 centimeters along the center line 211 as the point 217'.

The image generator 14 generates a VE image from a line of sight travelling from the point 217' to the stenosis region 212. The image generator 14 sequentially generates new VE images by shifting the viewpoint position from the point 217' to the point 214. In this manner, an operator is allowed to make observations focusing on the fly-through view around the stenosis region 212. In the third embodiment, a plurality of abnormal cross sections may also be detected.

Figure 16:
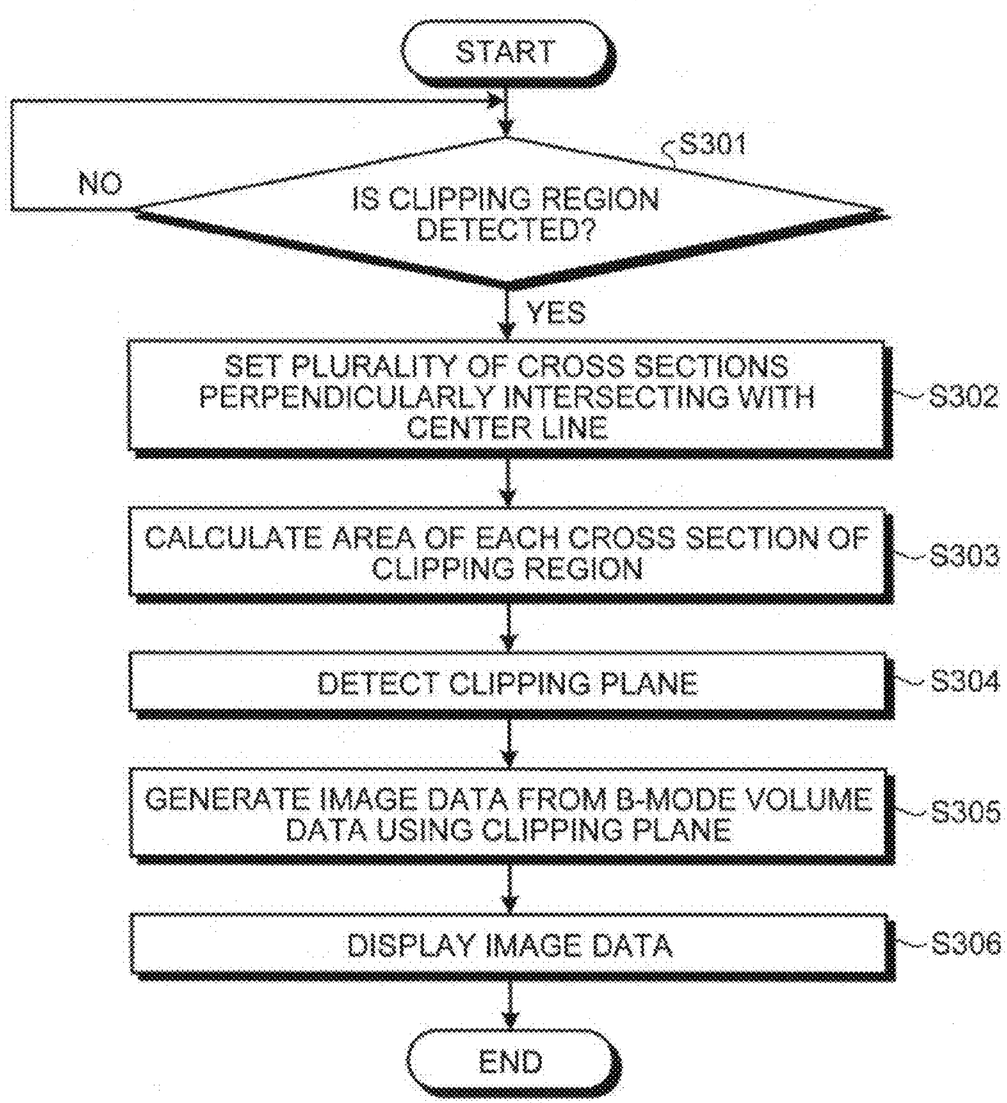
FIG. 16 is a flowchart for explaining an exemplary process performed by the ultrasonic diagnostic apparatus according to the third embodiment.

A process performed by the ultrasonic diagnostic apparatus according to the third embodiment will now be explained with reference to FIG. 16. FIG. 16 is a flowchart for explaining an exemplary process performed by the ultrasonic diagnostic apparatus according to the third embodiment. The flowchart illustrated in FIG. 16 is performed when an abnormal cross section serving as a clipping plane is automatically detected after the clipping region is detected. Alternatively, in the third embodiment, an operator may issue a request for detecting a clipping plane manually.

As illustrated in FIG. 16, the ultrasonic diagnostic apparatus according to the third embodiment determines if a clipping region is detected (Step S301). If any clipping region is not detected (No at Step S301), the ultrasonic diagnostic apparatus waits until a clipping region is detected.

If a clipping region is detected (Yes at Step S301), the detecting unit 16*b* sets a plurality of cross sections perpendicularly intersecting with the center line (Step S302). The detecting unit 16*b* then calculates the area of each of the cross sections of the clipping region (Step S303), and detects an abnormal cross section to be served as a clipping plane (Step S304).

The image generator 14 then generates image data to be displayed from the B-mode volume data using the clipping plane (Step S305). The monitor 2 then displays the image data under the control of the controller 16 (Step S306), and the process is ended.

As described above, in the third embodiment, a region where a stenosis or an aneurysm is formed can be detected easily as an abnormal cross section using a clipping region. Furthermore, in the third embodiment, because various types of image data are generated using an abnormal cross section as a clipping plane, abnormalities in the shape of a lumen such as a blood vessel can be observed in detail.

Therefore, in the third embodiment, precision of a diagnosis of abnormalities in the shapes of a blood vessel using an ultrasonic diagnostic apparatus, which is characterized by non-invasiveness, and examination efficiency can be improved.

Explained in the first embodiment to the third embodiment is an example in which B-mode volume data is used as the tissue volume data, and power volume data or color Doppler data is used as the fluid volume data. Alternatively, in the first embodiment to the third embodiment, three-dimensional B-mode data may be used as the tissue volume data, and three-dimensional Doppler data may be used as the fluid volume data. In such a case, the detecting unit 16*b* detects a clipping region in the three-dimensional B-mode data, using the power in the three-dimensional Doppler data, and detects a clipping region in the B-mode volume data using the clipping region thus detected.

Furthermore, the image processing methods explained in the first embodiment to the third embodiment may be executed in a manner described in the following two variations (first variation and second variation).

The first variation will be explained to begin with. Explained in the first embodiment to the third embodiment is an example in which the tissue volume data used as the volume data to be applied with the image processing is tissue volume data generated by scanning a region (a scan region) from which fluid volume data is collected three-dimensionally with ultrasound. The image processing methods explained in the first embodiment to the third embodiment are also applicable to an embodiment in which the tissue volume data used as the volume data to be applied with the image processing is tissue volume data generated by three-dimensionally capturing the region (the scan region), from which fluid volume data is collected, with a different type of a medical image diagnostic apparatus other than an ultrasonic diagnostic apparatus. In the first variation, the acquiring unit 16*a* acquires the tissue volume data generated by capturing images of a region from which fluid volume data is collected three-dimensionally using a different type of a medical image diagnostic apparatus other than an ultrasonic diagnostic apparatus.

In the first variation, the detecting unit 16*b* detects the inner cavity region of a lumen included in the tissue volume data after registration the fluid volume data and the tissue volume data.

Figure 17:
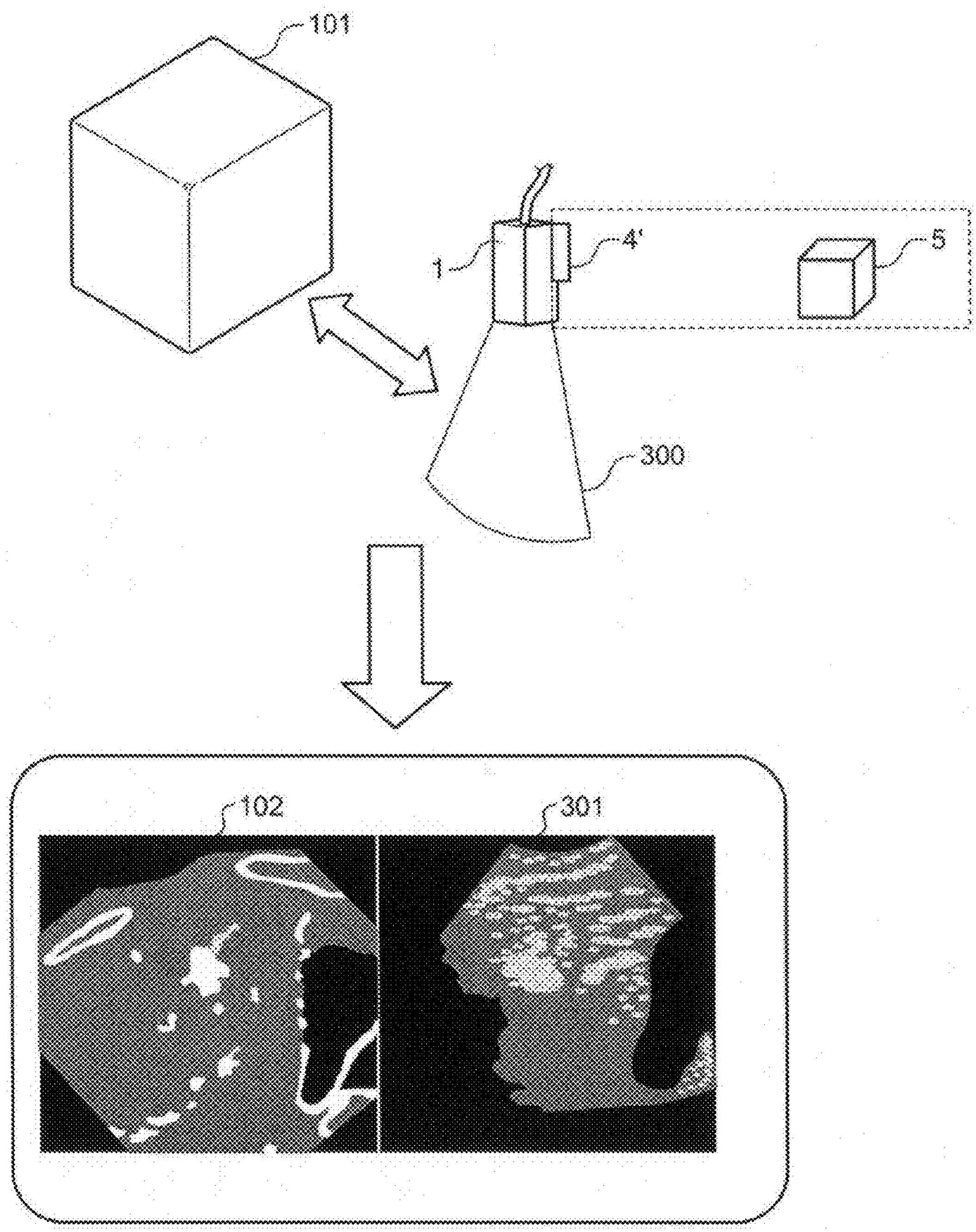
FIG. 17 is a schematic for explaining a first variation.

FIG. 17 is a schematic for explaining the first variation. For example, the acquiring unit 16*a* acquires X-ray CT volume data 101, as illustrated in FIG. 17. The acquiring unit 16*a* acquires the X-ray CT volume data 101 from an X-ray CT apparatus or a database of medical images via an interface not illustrated, based on an operator instruction. The X-ray CT volume data 101 is a piece of tissue volume data capturing a region from which fluid volume data is collected. Specifically, the X-ray CT volume data 101 is tissue CT volume data to be used in a fly-through view with VE images and designated by an operator.

When the first variation is implemented, a position detecting system utilizing a position sensor 4' and a transmitter 5 are used, as illustrated in FIG. 17, for example. The position sensor 4' is a magnetic sensor, for example, and is mounted on the ultrasonic probe 1. The transmitter 5 is a device that is positioned near the ultrasonic probe 1, and generates a magnetic field outwardly from the transmitter 5, for example.

The position sensor 4' detects a three-dimensional magnetic field generated by the transmitter 5. The position sensor 4' then calculates the position (coordinates and angle) of the position sensor 4' in a space having the point of origin at the transmitter 5, based on the information of the magnetic field thus detected, and transmits the position thus calculated to the detecting unit 16*b*. The position sensor 4' transmits the three-dimensional coordinates and the angle at which the position sensor 4' is positioned to the detecting unit 16*b* as the three-dimensional position information of the ultrasonic probe 1. In this manner, the detecting unit 16*b* acquires the three-dimensional position information of the ultrasonic probe 1.

An operator performs B-mode ultrasonic scanning in a region including a lumen of the subject P. For example, the operator performs two-dimensional scanning of the subject P across a cross section 300 using the ultrasonic probe 1, as illustrated in FIG. 17. The cross section 300 is set as a cross section positioned at the center of the three-dimensionally scanned region, for example. The controller 16 controls transmissions and receptions of ultrasound via the transmitter-receiver 11. In this manner, the detecting unit 16*b* can acquire the relative position of the cross section 300 with respect to the ultrasonic probe 1. Furthermore, the detecting unit 16*b* can acquire the three-dimensional position information of the cross section 300 in the real space, because the three-dimensional position information of the ultrasonic probe 1 is acquired.

The monitor 2 displays two-dimensional B-mode image data 301 generated by two-dimensionally scanning the cross section 300, as illustrated in FIG. 17. The operator operates the ultrasonic probe 1 on which the position sensor 4' is mounted so that the lumen of the subject P to be captured in the VE images is represented at an approximate center of the image, while looking at the B-mode image data 301 displayed on the monitor 2. The operator also adjust the position of the cross section to be used for an MPR process via the input device 3, so that the X-ray CT image data representing the lumen of the subject P is displayed on the monitor 2. The monitor 2 then displays an MPR image data 102 of the X-ray CT volume data 101, as illustrated in FIG. 17.

When the same feature part as the feature part represented in the MPR image data 102 is represented in the B-mode image data 301, the operator presses an OK button. The operator then designates the center position of the feature part in each of these images using a mouse. Alternatively, the operator may designate the position of a plurality of feature parts in each of these images using a mouse. The operator then performs three-dimensional scanning of the subject P in the Doppler mode in a three-dimensional region including the cross section 300 at the time the OK button was pressed, to collect the fluid volume data.

The image generator 14 then generates the fluid volume data (e.g., power volume data). The detecting unit 16*b* performs registration the fluid volume data and the X-ray CT volume data 101, using various types of information of when the OK button was pressed. Various types of information of when the OK button was pressed include three-dimensional position information of the cross section in the X-ray CT volume data 101 corresponding to the MPR image data 102 of when the OK button was pressed, and three-dimensional position information of the cross section 300 in the real space corresponding to the B-mode image data 301 of when the OK button was pressed. The detecting unit 16*b* converts the three-dimensional position information of the cross section 300 in the real space into the three-dimensional position information of the cross section 300 in the fluid volume data, based on ultrasound transmitting and receiving conditions and conditions for scan conversions. Various types of information of when the OK button was pressed also includes the position information of a feature part included in each of the MPR image data 102 and the B-mode image data 301. For example, the detecting unit 16*b* generates a conversion matrix for converting the coordinate system of the fluid volume data into the coordinate system of the X-ray CT volume data 101 using these various types of information.

In the first variation, the detecting unit 16*b* may perform registration the B-mode volume data collected from the same temporal phase as the fluid volume data and another type of tissue volume data using three or more feature regions designated by the operator. Furthermore, the detecting unit 16*b* may perform registration the B-mode volume data collected from the same temporal phase as the fluid volume data and another type of tissue volume data using edge detection or feature point detection, for example. By means of these detections, the detecting unit 16*b* can perform registration the fluid volume data and the other type of tissue volume data.

The detecting unit 16*b* then detects a fluid region (a fluid existing region) in the fluid volume data, as explained in the first embodiment. The detecting unit 16*b* then converts the three-dimensional position information of the fluid region into the three-dimensional position information of the X-ray CT volume data 101 using the above-described conversion matrix, for example. Such three-dimensional position information represents the inner cavity region of a lumen in the X-ray CT volume data 101. The image generator 14 generates VE images for a fly-through view from the X-ray CT volume data 101, by performing the process explained in the first embodiment with reference to FIG. 6. The image generator 14 may generates various types of image data explained in the first embodiment with reference to FIGS. 7A, 7B, and 7C from the X-ray CT volume data 101.

In the first variation as well, when another type of tissue volume data and the fluid volume data are collected sequentially, as explained in the second embodiment, the acquiring unit 16*a* acquires the other type of tissue volume data and the fluid volume data from the same temporal phase using a biological signal of the subject P. The detecting unit 16*b* then detects the inner cavity region after registration the other type of tissue volume data and the fluid volume data from the same temporal phase.

In the first variation as well, as explained in the third embodiment, the detecting unit 16*b* may detect an abnormal cross section in the other type of tissue volume data. Furthermore, in the first variation as well, as explained in the third embodiment, the image generator 14 may generate image data to be displayed on the monitor 2 from the other type of tissue volume data using the abnormal cross section.

According to the first variation, the inner cavity region of a lumen in non-contrast X-ray CT volume data, non-contrast MRI volume data, or the like can be detected easily using the fluid volume data.

Figure 18:
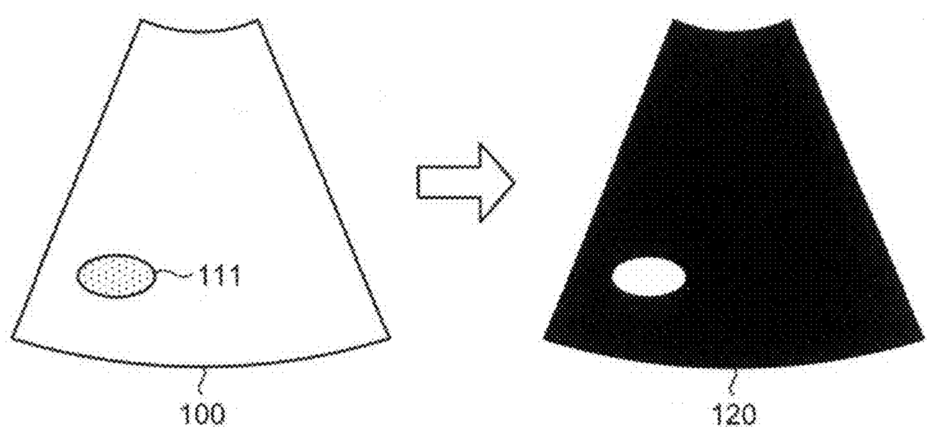
FIG. 18 is a schematic for explaining a second variation.

A second variation will now be explained with reference to FIG. 18 and the like. FIG. 18 is a schematic for explaining the second variation. In the second variation, the fluid volume data is used as volume data to be applied with the image processing. In the second variation, the acquiring unit 16*a* acquires fluid volume. The detecting unit 16*a* detects a fluid region detected in the fluid volume data as the inner cavity region of a lumen in the fluid volume data.

For example, the detecting unit 16*b* detects the fluid region 110 in the power volume data 100, as illustrated in FIG. 2. The detecting unit 16*b* then detects the fluid region 110 as an inner cavity region 111 of the lumen in the power volume data 100, as illustrated in the left drawing in FIG. 18. In the left drawing in FIG. 18, the power volume data 100 and the inner cavity region 111 are illustrated as two-dimensional data, but in practice, the power volume data 100 and the inner cavity region 111 are three-dimensional data.

In the left drawing in FIG. 18, the inner cavity region 111 that is the fluid region 110 assigned with a luminance is represented as hatched, and the region with no fluid (the region other than the inner cavity region 111 in the power volume data 100) is represented in white.

In the second variation, the image generator 14 generates simulated volume data from the fluid volume data using the inner cavity region detected by the detecting unit 16*b*. Specifically, the image generator 14 removes the inner cavity region detected by the detecting unit 16*b* from the fluid volume data. The image generator 14 then assigns a predetermined luminance at least to the inner wall of the lumen based on the inner cavity region detected by the detecting unit 16*b*.

For example, the image generator 14 assigns a luminance "0" to the inner cavity region 111, and assigns a luminance "1" to the region other than the inner cavity region 111 in the power volume data 100. As a result, the image generator 14 generates simulated volume data 120 in which the inner cavity region 111 is removed, and the voxels corresponding to the inner wall of the lumen is assigned with luminance "1" (see the right drawing in FIG. 18). In the right drawing in FIG. 18, the simulated volume data 120 is illustrated as two-dimensional data, but in practice, the simulated volume data 120 is three-dimensional data. In the right drawing in FIG. 18, the region assigned with the luminance "1", that is, the region without any fluid such as the inner wall of a lumen is represented in black. In the right drawing in FIG. 18, the region assigned with the luminance "0", that is, the inner cavity region 111 thus removed, is represented in white. The image generator 14 may also generate the simulated volume data 120 by assigning luminance "1" only to the inner wall of the lumen and to the region near the inner wall in the region other than the inner cavity region 111 in the power volume data 100, for example.

The image generator 14 then generates projected images (VE images) in which the simulated volume data 120 is projected from the viewpoint positions set inside of the lumen as the image data to be displayed on the monitor 2. The image generator 14 then extracts the center line of the lumen from the simulated volume data 120. The image generator 14 generates dynamic images including a plurality of projected images (VE images) in which the viewpoint position is shifted along the center line, as the image data group to be displayed on the monitor 2.

In the second variation as well, the detecting unit 16*b* may detect an abnormal cross section from the simulated volume data 120 generated from the power volume data 100 which is the volume data to be applied with the image processing, as explained in the third embodiment. Furthermore, in the second variation as well, as explained in the third embodiment, the image generator 14 may generate image data to be displayed on the monitor 2 from the simulated volume data 120 using an abnormal cross section.

In the second variation, a fly-through view can be provided using only the Doppler volume data (fluid volume data), from which the inner cavity region of a lumen can be easily detected.

Furthermore, the image processing methods explained in the first embodiment to the third embodiment, the first variation, and the second variation may be executed by an image processing apparatus deployed independently from the ultrasonic diagnostic apparatus. Such an image processing apparatus can execute the image processing methods explained in the first embodiment to the third embodiment by acquiring three-dimensional B-mode data and three-dimensional Doppler data, or B-mode volume data and Doppler volume data. Furthermore, the image processing apparatus can execute the image processing methods explained in the first variation by acquiring three-dimensional Doppler data or Doppler volume data, another type of tissue volume data, and registration information (for example, conversion matrix). Furthermore, such an image processing apparatus can execute the image processing method explained in the second variation by acquiring three-dimensional Doppler data or Doppler volume data.

The units included in the apparatuses illustrated in the drawings are provided as schematic representations of the corresponding concepts and functionality, and are not required to be physically configured in the manner illustrated in the drawings. Specific configurations in which the apparatuses are distributed or integrated are not limited to those illustrated in the drawings, and the whole or a part of the apparatuses may be distributed or integrated functionally or physically in any units depending on various loads or utilization. Furthermore, the whole or a part of the processing functions executed in each of the apparatuses may be realized as a central processing unit (CPU) and a computer program parsed and executed by the CPU, or realized as hardware using wired logics.

Each of the image processing methods explained in the first embodiment to the third embodiment, the first variation, and the second variation can be realized by causing a computer such as a personal computer or a workstation to execute an image processing program prepared in advance. Such an image processing program may be distributed over a network such as the Internet. Furthermore, the control program may be recorded in a computer-readable non-temporary recording medium such as a hard disk, a flexible disk (FD), a compact disk read-only memory (CD-ROM), a magneto-optical (MO) disk, a digital versatile disk (DVD), or a flash memory such as a universal serial bus (USB) memory or a Secure Digital (SD) card memory, and executed by being read from the recording medium.

As explained above, according to the first embodiment to the third embodiment, the first variation, and the second variation, the inner cavity region of a lumen can be detected easily.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus, comprising:

processing circuitry configured to acquire fluid volume data representing fluid information related to a fluid flowing through a scan region that is a region three-dimensionally scanned by ultrasonic waves;

acquire tissue volume data representing a tissue form in the scan region;

detect a fluid existing region in which fluid is flowing in the scan region using the fluid information, and detect an inner cavity region of a lumen included in the tissue volume data using the detected fluid existing region;

generate a projected image in which the tissue volume data is projected from a viewpoint position set inside of the lumen, based on the detected inner cavity region, as image data to be displayed on a display;

calculate an area of the inner cavity region in each of a plurality of cross sections perpendicularly intersecting with a center line of the inner cavity region; and detect a cross section having a calculated area deviating from those calculated for nearby cross sections as an abnormal cross section.

2. The ultrasonic diagnostic apparatus according to claim 1, wherein the processing circuitry is further configured to extract a center line of the lumen from data in which the inner cavity region is removed from the tissue volume data, and generate a plurality of projected images by shifting a viewpoint position along the center line as an image data group to be displayed as dynamic images on the display.

3. The ultrasonic diagnostic apparatus according to claim 1, wherein the processing circuitry is further configured to, when the tissue volume data and the fluid volume data are collected separately and sequentially at different times, acquire tissue volume data and fluid volume data from a same temporal phase using a biological signal of a subject from whom the tissue volume data and the fluid volume data are collected, and detect the inner cavity region using the tissue volume data and the fluid volume data from the same temporal phase.

4. The ultrasonic diagnostic apparatus according to claim 1, wherein the processing circuitry is further configured to acquire volume data generated by three-dimensional ultrasonic-scanning of the scan region as the tissue volume data.

5. The ultrasonic diagnostic apparatus according to claim 1, wherein the processing circuitry is further configured to acquire volume data generated by three-dimensionally capturing the scan region with a medical image diagnostic apparatus of a type different from the ultrasonic diagnostic apparatus as the tissue volume data, and detect the inner cavity region of the lumen included in the tissue volume data after registering the fluid volume data and the tissue volume data.

6. The ultrasonic diagnostic apparatus according to claim 1, wherein the processing circuitry is further configured to generate image data to be displayed on the display from the tissue volume data, using the abnormal cross section.

7. The ultrasonic diagnostic apparatus of claim 1, further comprising an ultrasonic probe configured to scan the region with the ultrasonic waves.

8. The ultrasonic diagnostic apparatus of claim 1, wherein the processing circuitry is configured to acquire power volume data as the fluid volume data in which the fluid information is power, and detect the fluid existing region as being those voxels having a power value exceeding a threshold.

9. The ultrasonic diagnostic apparatus of claim 1, wherein the fluid volume data is obtained from a Doppler mode scan and the tissue volume data is obtained from a B-mode scan.

10. An ultrasonic diagnostic apparatus, comprising:

processing circuitry configured to acquire fluid volume data representing fluid information related to a fluid flowing through a scan region that is a region three-dimensionally scanned by ultrasonic waves, detect a fluid existing region in the scan region as an inner cavity region of a lumen in the fluid volume data using the fluid information, remove the detected inner cavity region, assign a given luminance at least to an inner wall of the lumen based on the detected inner cavity region, and generate simulated volume data from the fluid volume data, and generate a projected image in which the simulated volume data is projected from a viewpoint position set inside of the lumen as image data to be displayed on a display.

11. The ultrasonic diagnostic apparatus according to claim 10, wherein the processing circuitry is further configured to extract a center line of the lumen from the simulated volume data, and generate a plurality of projected images by shifting the viewpoint position along the center line as an image data group to be displayed as dynamic images on the display.

12. An image processing apparatus, comprising:

processing circuitry configured to acquire fluid volume data representing fluid information related to a fluid flowing through a scan region that is a region three-dimensionally scanned by ultrasonic waves;

acquire tissue volume data representing a tissue form in the scan region;

detect a fluid existing region in which fluid is flowing in the scan region using the fluid information, and detect an inner cavity region of a lumen included in volume data using the detected fluid existing region;

generate a projected image in which the tissue volume data is projected from a viewpoint position set inside of the lumen, based on the detected inner cavity region, as image data to be displayed on a display;

calculate an area of the inner cavity region in each of a plurality of cross sections perpendicularly intersecting with a center line of the inner cavity region; and detect a cross section having a calculated area deviating from those calculated for nearby cross sections as an abnormal cross section.

13. An image processing method, comprising:

acquiring, by processing circuitry, fluid volume data representing fluid information related to a fluid flowing through a scan region that is a region three-dimensionally scanned by ultrasonic;

acquiring, by the processing circuitry, tissue volume data representing a tissue form in the scan region;

detecting, by the processing circuitry, a fluid existing region in which fluid is flowing in the scanned region using the fluid information, and an inner cavity region of a lumen included in the tissue volume data using the detected fluid existing region;

generating a projected image in which the tissue volume data is projected from a viewpoint position set inside of the lumen, based on the inner cavity region, as image data to be displayed on a display;

calculating an area of the inner cavity region in each of a plurality of cross sections perpendicularly intersecting with a center line of the inner cavity region; and detecting a cross section having a calculated area deviating from those calculated for nearby cross sections as an abnormal cross section.

14. An image processing apparatus, comprising:

processing circuitry configured to acquire fluid volume data representing fluid information related to a fluid flowing through a scan region that is a region three-dimensionally scanned by ultrasonic waves, detect a fluid existing region in the scan region as an inner cavity region of a lumen in the fluid volume data using the fluid information, remove the detected inner cavity region, assign a given luminance at least to an inner wall of the lumen based on the detected inner cavity region, and generate simulated volume data from the fluid volume data, and generate a projected image in which the simulated volume data is projected from a viewpoint position set inside of the lumen as image data to be displayed on a display.

15. An image processing method, comprising:

acquiring fluid volume data representing fluid information related to a fluid flowing through a scan region that is a region three-dimensionally scanned by ultrasonic waves;

detecting a fluid existing region in the scan region as an inner cavity region of a lumen in the fluid volume data using the fluid information;

removing the detected inner cavity region, assigning a given luminance at least to an inner wall of the lumen based on the detected inner cavity region, and generating a simulated volume data from the fluid volume data; and generating a projected image in which the simulated volume data is projected from a viewpoint position set inside of the lumen as image data to be displayed on a display.

* * * * *